(12) United States Patent
Kumar et al.

(10) Patent No.: US 7,041,812 B2
(45) Date of Patent: May 9, 2006

(54) LABELED NUCLEOSIDE POLYPHOSPHATES

(75) Inventors: Shiv Kumar, Belle Mead, NJ (US); Anup Sood, Flemington, NJ (US)

(73) Assignee: Amersham Biosciences Corp, Piscataway, NJ (US)

( * ) Notice: Subject to any disclaimer, the term of this patent is extended or adjusted under 35 U.S.C. 154(b) by 300 days.

(21) Appl. No.: 10/230,576

(22) Filed: Aug. 29, 2002

(65) Prior Publication Data

US 2003/0124576 A1    Jul. 3, 2003

Related U.S. Application Data

(60) Provisional application No. 60/315,798, filed on Aug. 29, 2001.

(51) Int. Cl.
| | |
|---|---|
| *C07H 21/00* | (2006.01) |
| *C07H 21/02* | (2006.01) |
| *C07H 21/04* | (2006.01) |
| *C12Q 1/68*  | (2006.01) |
| *C12P 19/34* | (2006.01) |

(52) U.S. Cl. ............... 536/23.1; 435/6; 435/91.1; 435/91.2; 536/24.3

(58) Field of Classification Search .......... 435/6, 435/91.1, 91.2; 536/23.1, 24.3
See application file for complete search history.

(56) References Cited

U.S. PATENT DOCUMENTS

| | | | | |
|---|---|---|---|---|
| 5,728,525 | A * | 3/1998 | Conrad ..................... | 435/6 |
| 5,849,487 | A | 12/1998 | Hase et al. | |
| 6,187,286 | B1 | 2/2001 | Elmaleh et al. | |
| 6,306,607 | B1 * | 10/2001 | Williams ................... | 435/6 |
| 2003/0064366 | A1 * | 4/2003 | Hardin et al. ............. | 435/6 |

FOREIGN PATENT DOCUMENTS

| | | |
|---|---|---|
| WO | WO 96/22297 | 7/1996 |
| WO | WO 99/16832 | 4/1999 |

(Continued)

OTHER PUBLICATIONS

Newton, C. R., et al. "The Production of PCR Products with 5' Single-Stranded Tails Using Primers that Incorporate Novel Phosphoramidite Intermediates" Nucleic Acid Research, Oxford University Press, Surrey, GB, vol. 21, No. 5, 1993, pp. 1155-1162.

(Continued)

*Primary Examiner*—Jezia Riley
(74) *Attorney, Agent, or Firm*—Yonggang Ji

(57) ABSTRACT

The present invention describes new compositions of matter in the form of labeled nucleoside polyphosphates with four or more phosphates. In addition compositions of nucleoside polyphosphates with four or more phosphates that are substrates for nucleic acid polymerases with enhanced substrate properties and methods of using these nucleoside polyphosphates for nucleic acid detection, characterization and quantification are described. The compositions provided by this invention include nucleoside polyphosphate, dideoxynucleoside polyphosphate, or deoxynucleoside polyphosphate analogues which have colorimetric, chemiluminescent, or fluorescent moieties, mass tags or an electrochemical tags attached to the terminal-phosphate. When a nucleic acid polymerase uses this analogue as a substrate, an enzyme-activatable label would be present on the inorganic polyphosphate by-product of phosphoryl transfer. Removal of the polyphosphate product of phosphoryl transfer via phosphate or polyphosphate transferring enzyme leads to a detectable change in the label attached thereon. When the polymerase assay is performed in the presence of a phosphatase, there is provided a convenient method for real-time monitoring of DNA or RNA synthesis and detection of a target nucleic acid.

31 Claims, 4 Drawing Sheets

Incorporation of polyphosphate DDAO-analogs of ddT by DNA Pol

FOREIGN PATENT DOCUMENTS

| WO | WO 02/40126 | 5/2002 |
|----|-------------|--------|
| WO | WO 03/020734 | 3/2003 |
| WO | WO 03/020891 | 3/2003 |

OTHER PUBLICATIONS

Dyatkina, N., et al. "Modified Triphosphates of carbocyclic nucleoside analogues: synthesis, stability towards alkaline phosphatase and substrate properties for some DNA polymerases" Bioorganic and Medicinal Chemistry Letters, Oxford, GB. vol. 6, No. 22, Nov. 19, 1996, pp. 2639-2642.

Su, S-H., et al. "Novel non-nucleosidic phosphoramidites for oligonucleotide modification and labeling" Bioorganic and Medicinal Chemistry Letters, Oxford, GB, vol. 7, No. 13, Jul. 8, 1997, pp. 1639-1644.

Arzumanov Andrey, A., et al. "Gamma-Phosphate-substituted 2'-deoxynucleoside 5'-triphosphates as substrates for DNA polymerases" Journal of Biological Chemistry, vol. 271, No. 40, 1996, pp. 24389-24394.

\* cited by examiner

Incorporation of polyphosphate DDAO-analogs of ddT by DNA Pol

Comparison of Tri and Tetra-phosphatedT-DDAO

Initial Rates:
(nM/sec)

DNA Pol:
dTTP 0.0065
dTQP 0.26
(40-fold)

MMLV:
dTTP 0.033
dTQP 0.58
(18-fold)

Tetraphosphate dideoxy-analogs increase activity by up to 15-fold resorufin

DDAO

SEQ ID NO: 1  5'-GTTCTCGGCATCACCATCCG-3'

SEQ ID NO: 2  3'-CAAGAGCCGTAGTGGTAGGCAGCCGTTGGTCTATTCCCAC-5'

SEQ ID NO: 3  3'-CAAGAGCCGTAGTGGTAGGCGGCCGTTGGTCTATTCCCAC-5'

SEQ ID NO: 4  3'-CAAGAGCCGTAGTGGTAGGCCGCCGTTGGTCTATTCCCAC-5'

SEQ ID NO: 5  3'-CAAGAGCCGTAGTGGTAGGCTGCCGTTGGTCTATTCCCAC-5'

Figure 4

SEQUENCE LISTING

```
<160> NUMBER OF SEQ ID NOS: 5

<210> SEQ ID NO 1
<211> LENGTH: 20
<212> TYPE: DNA
<213> ORGANISM: artificial sequence
<220> FEATURE:
<223> OTHER INFORMATION: synthetic oligonucleotide

<400> SEQUENCE: 1
gttctcggca tcaccatccg                                                   20

<210> SEQ ID NO 2
<211> LENGTH: 40
<212> TYPE: DNA
<213> ORGANISM: artificial sequence
<220> FEATURE:
<223> OTHER INFORMATION: synthetic oligonucleotide
```

```
-continued

<400> SEQUENCE: 2
caagagccgt agtggtaggc agccgttggt ctattcccac                              40

<210> SEQ ID NO 3
<211> LENGTH: 40
<212> TYPE: DNA
<213> ORGANISM: artificial sequence
<220> FEATURE:
<223> OTHER INFORMATION: synthetic oligonucleotide

<400> SEQUENCE: 3
caagagccgt agtggtaggc ggccgttggt ctattcccac                              40

<210> SEQ ID NO 4
<211> LENGTH: 40
<212> TYPE: DNA
<213> ORGANISM: artificial sequence
<220> FEATURE:
<223> OTHER INFORMATION: synthetic oligonucleotide

<400> SEQUENCE: 4
caagagccgt agtggtaggc cgccgttggt ctattcccac                              40

<210> SEQ ID NO 5
<211> LENGTH: 40
<212> TYPE: DNA
<213> ORGANISM: artificial sequence
<220> FEATURE:
<223> OTHER INFORMATION: synthetic oligonucleotide

<400> SEQUENCE: 5
caagagccgt agtggtaggc tgccgttggt ctattcccac                              40
```

LABELED NUCLEOSIDE POLYPHOSPHATES

This application is a provisional of Ser. No. 60/315,798 filed Aug. 29, 2001.

FIELD OF INVENTION

The present invention relates generally to compositions of matter of terminal-phosphate-labeled nucleotides including four or more phosphates. It has been found by the inventors that increasing the number of phosphate units of a terminal-phosphate-labeled nucleoside polyphosphate from three to 4 or more increases their incorporation efficiency by polymerases. The labels employed are chemiluminescent, fluorescent, electrochemical and chromophoric moieties as well as mass tags and include those that are directly detectable, detectable after enzyme activation or feed into other processes to generate a different signal. Also disclosed are methods of using these nucleotides by nucleic acid polymerases for detection, characterization or quantification of DNA or RNA.

BACKGROUND OF INVENTION

Methods are known for detecting specific nucleic acids or analytes in a sample with high specificity and sensitivity. Such methods generally require first amplifying nucleic acid sequence based on the presence of a specific target sequence or analyte. Following amplification, the amplified sequences are detected and quantified. Conventional detection systems for nucleic acids include detection of fluorescent labels, colored dyes, fluorescent enzyme-linked detection systems, antibody-mediated label detection, and detection of radioactive labels.

One disadvantage of detection methods presently widely in use is the need to separate labeled starting materials from a final labeled product or by-product. Such separations generally require gel electrophoresis or immobilization of a target sequence onto a membrane for detection. Moreover, there are often numerous reagents and/or incubation steps required for detection.

It has been known that DNA and RNA polymerases are able to recognize and utilize nucleosides with a modification at or in place of the gamma position of the triphosphate moiety. It is further known that the ability of various polymerases to recognize and utilize gamma-modified nucleotide triphosphates (NTP's) appears to vary depending on the moiety attached to the gamma phosphate. In general, RNA polymerases are more promiscuous than DNA polymerases. Still, the efficiency of incorporation is significantly reduced compared to normal nucleotides. Even with this limitation, a number of potential applications using γ-labeled nucleoside triphosphates have been described in the literature.

A colorimetric assay for monitoring RNA synthesis from RNA polymerases in presence of a gamma-phosphate modified nucleotide has been previously reported (Vassiliou W et. al., Exploiting polymerase promiscuity: A simple calorimetric RNA polymerase assay, Virology. 2000 Sep. 1; 274(2): 429–37; C. C. Kao et. al, U.S. Pat. No. 6,399,335 B1). In this prior report, RNA polymerase reactions were performed in the presence of a gamma-modified, alkaline phosphatase resistant nucleotide triphosphate which was modified at its gamma-phosphate with a dinitrophenyl group. When RNA polymerase reactions were performed in the presence of this gamma-modified NTP as the sole nucleotide triphosphate and a homopolymeric template, it was found that RNA polymerase could recognize and utilize the modified NTP. Moreover, when the polymerase reactions were performed in the presence of an alkaline phosphatase, which digested the p-nitrophenyl pyrophosphate aldo-product of phosphoryl transfer to the chromogenic p-nitrophenylate, an increase in absorbence was reported.

A number of references in the patent literature describe the use of γ-labeled nucleotides for DNA detection and sequencing (Hardin et. al., WO02/44425 A2, Williams, J. G. WO 00/36151 and WO 00/36152). Williams describes their use in single molecule detection of fluorescently labeled pyrophosphate being released after incorporation by polymerases. Attachment of a quencher to the base moiety allows for a homogeneous polymerase extension reaction where the amount of fluorescence in sample increases with incorporation of gamma labeled nucleoside triphosphate. Hardin et. al. further show their use in nucleic acid synthesis with a number of different polymerases. The efficiency of incorporation varies with polymerase used. Other reports (Felicia et. al., Arch. Biochem Biophys, 1986, 246, 564–571) describe the use of an γ-1,5-EDANS-ATP derivative as a substrate for E.Coli RNA polymerase. These references clearly point out the great potential that exists for the use of terminal phosphate labeled nucleotides. Unfortunately, despite the known potential uses, they have not been utilized in any major commercial applications.

As mentioned above, a major disadvantage with the use of γ-labeled nucleoside triphosphates in sequencing, SNP analysis and other assays is their poor acceptabilty by polymerases and other NTP utilizing enzymes. The reasons for this are probably multifold and may include the steric interactions between the gamma modification and certain amino acid residues in the enzyme pocket, and reduced metal binding by nucleotide or reduced electrostatic interactions between the nucleotide and polymerase due to one less negative charge on the nucleotide. It would, therefore, be of benefit to provide terminal labeled nucleoside polyphosphates where the label is further removed from the nucleoside by addition of additional phosphate groups, which also provide additional charges for metal binding or electrostatic interactions.

Nucleoside polyphosphates having a terminal modification and more than three phosphates are known in the literature. These are mainly dinucleoside polyphosphates (WO 01/12644 A1, U.S. Ser. No. 05/681,823, U.S. Ser. No. 05/663,322, U.S. Ser. No. 05/049,550, U.S. Ser. No. 05/658,890, U.S. Ser. No. 05/306,629, U.S. Ser. No. 04/886,749 and U.S. Ser. No. 6/183,978) where the modification on the terminal phosphate is the addition of another nucleoside. None of these have a label on the terminal phosphate. The only example of a nucleoside polyphosphate with a moiety on the terminal phosphate designed for detection and having four phosphate units that inventors are aware of is 5-bromo-4-chloro-3-indolyl tetraphospho-5'-adenosine. This compound has been used as a chromogenic substrate to investigate the activity of Ap4A phosphorylase and Ap4A hydrolases. In this case, detection was only possible after the tetraphosphate cleavage products were dephosphorylated and the indole moiety was oxidized in presence of nitro blue tetrazolium to give a colored dimer. This process requires at least two molecules of 5-bromo-4-chloro-3-hydroxyindole to generate a signal. At very low concentrations and especially for single molecule detection, this moiety is not useful. Thus, there is a need for terminal phosphate labeled nucleoside polyphosphates with readily detectable labels and which are better substrates for nucleic acid polymerases.

It would further be of benefit to provide nucleoside polyphosphates that are substrates for polymerases where the label on the terminal-phosphate could be varied so as to allow for chemiluminescent and fluorescent detection, analysis by mass or reduction potential, as well as for improved calorimetric detection, wherein only routine methods and instrumentation would be required for detection.

Given that DNA polymerases are known in the art to be less promiscuous than RNA polymerases regarding recognition and utilization of terminally-modified nucleotides, wherein the identity of the moiety at the terminal position can largely affect the DNA polymerase's specificity toward the nucleotide, it would be highly desired to provide for a non-radioactive method for detecting DNA by monitoring DNA polymerase activity. Furthermore, it would be desired that the synthesis and detection of DNA could be accomplished in a single-tube assay for real-time monitoring and that the label at the terminal-phosphate of nucleotide substrates could encompass chemiluminescent, fluorescent, and calorimetric detection, as well as analysis by mass or reduction potential.

SUMMARY OF INVENTION

The present invention provides new compositions of matter in the form of terminal phosphate labeled nucleoside polyphosphates of formula 1, with more than three phosphates where the label is a fluorescent, a chemiluminescent, a colored moiety or an electrochemical tag that is detectable with or without separation after cleavage from the nucleoside polyphosphate.

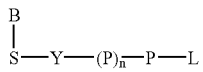

wherein P=phosphate ($PO_3$) and derivatives thereof, n is 3 or greater; Y is an oxygen or sulfur atom; B is a nitrogen-containing heterocyclic base; S is an acyclic moiety, carbocyclic moiety or sugar moiety; L is a fluorescent, a chemiluminescent, a colored, or an electrochemical label containing a hydroxyl group, a sulfhydryl group, a haloalkyl group or an amino group suitable for forming a phosphate ester, a thioester, an alkylphosphonate or a phosphoramidate linkage at the terminal phosphate of a natural or modified nucleotide; P-L is a phosphorylated label which preferably becomes independently detectable when the phosphate is removed.

The present invention further provides compositions of matter in the form of terminal phosphate labeled nucleoside polyphosphates with more than three phosphates, which are substrates for nucleic acid polymerases and where the label is a fluorescent, a luminescent, a colored dye or an electrochemical or mass tag.

The present invention provides for a method of detecting the presence of a nucleic acid sequence including the steps of: a) conducting a nucleic acid polymerase reaction, wherein the reaction includes the reaction of at least one nucleotide which is substantially non-reactive to phosphatase and at least one terminal-phosphate-labeled nucleotide of current invention, which reaction results in the production of labeled polyphosphate; b) permitting the labeled polyphosphate to react with a phosphatase or a phosphate or polyphosphate transferring enzyme, or a combination thereof, to produce a detectable species; and c) detecting the presence of the detectable species. A definition of phosphatase in the current invention includes any enzyme which cleaves phosphate mono esters, polyphosphates and nucleotides to release inorganic phosphate. Phosphate or polyphosphate transferring enzymes are those that transfer phosphate or polyphosphate moiety from one organic moiety to another and include, but are not limited to, pyrophosphatases, phosphoramidate phosphotransferases and triphosphatases. In the context of the present invention, these enzyme do not cleave a terminally labeled nucleoside phosphate (i.e. the terminal-phosphate-labeled nucleotide is substantially non-reactive to phosphatase or phosphate or polyphosphate transferring enzymes). The phosphatase definition herein provided specifically includes, but is not limited to, alkaline phosphatase (EC 3.1.3.1) and acid phosphatase (EC 3.1.3.2). The definition of a nucleotide in the current invention includes a natural or modified nucleoside phosphate.

The present invention further provides for a method of detecting the presence of a nucleic acid sequence including the steps of: a) conducting a nucleic acid polymerase reaction, wherein the reaction includes the reaction of at least one terminal-phosphate-labeled nucleotide of current invention, which reaction results in the production of labeled polyphosphate; b) detecting the presence of the labeled polyphosphate with or without separation.

The invention further provides for a method of detecting the presence of a DNA sequence including the steps of: a) conducting a DNA polymerase reaction in the presence of a terminal-phosphate-labeled nucleotide of current invention, which reaction results in the production of a labeled polyphosphate; b) permitting the labeled polyphosphate to react with a phosphatase or phosphate or polyphosphate transferring enzyme to produce a detectable species; and c) detecting the presence of the detectable species.

The present invention provides for a method of detecting the presence of a DNA sequence including the steps of: a) conducting a nucleic acid polymerase reaction, wherein the reaction includes the reaction of at least one terminal-phosphate-labeled nucleotide of current invention, which reaction results in the production of labeled polyphosphate; b) detecting the presence of labeled polyphosphate with or without separation.

A further aspect of the present invention relates to a method of quantifying a nucleic acid including the steps of: (a) conducting a nucleic acid polymerase reaction, wherein the reaction includes the reaction of a nucleotide which is substantially non-reactive to phosphatase and at least one terminal-phosphate-labeled nucleotide of current invention, which reaction results in production of labeled polyphosphate; (b) permitting the labeled polyphosphate to react with a phosphatase or phosphate or polyphosphate transferring enzyme to produce a detectable by-product species in an amount substantially proportional to the amount of nucleic acid; (c) measuring the detectable species; and (d) comparing the measurements using known standards to determine the quantity of nucleic acid.

The present invention provides for a method of quantifying a nucleic acid sequence including the steps of: a) conducting a nucleic acid polymerase reaction, wherein the reaction includes the reaction of at least one terminal-phosphate-labeled nucleotide of current invention, which reaction results in the production of labeled polyphosphate in an amount substantially proportional to the amount of nucleic acid; b) measuring the amount of labeled polyphosphate with or without separation, and comparing the measurements using known standards to determine the quantity of nucleic acid.

The invention further relates to a method of quantifying a DNA sequence including the steps of: (a) conducting a DNA polymerase reaction in the presence of a terminal-phosphate-labeled nucleotide of current invention, the reaction resulting in production of labeled polyphosphate; (b) permitting the labeled polyphosphate to react with a phosphatase or phosphate or polyphosphate transferring enzyme to produce a detectable by-product species in amounts substantially proportional to the amount of the DNA sequence; (c) measuring the detectable species; and (d) comparing the measurements using known standards to determine the quantity of DNA.

The present invention provides for a method of quantifying a DNA sequence including the steps of: a) conducting a nucleic acid polymerase reaction, wherein the reaction includes the reaction of at least one terminal-phosphate-labeled nucleotide of current invention, which reaction results in the production of labeled polyphosphate in an amount substantially proportional to the amount of nucleic acid; b) measuring the amount of labeled polyphosphate with or without separation, and comparing the measurements using known standards to determine the quantity of DNA.

Another aspect of the invention relates to a method for determining the identity of a single nucleotide in a nucleic acid sequence, which includes the steps of: (a) conducting a nucleic acid polymerase reaction in the presence of at least one terminal phosphate-labeled nucleotide, which reaction results in the production of labeled polyphosphate; (b) permitting the labeled polyphosphate to react with a phosphatase or phosphate or polyphosphate transferring enzyme to produce a detectable species; (c) detecting the presence of the detectable species; and (d) identifying the nucleoside incorporated.

Another aspect of the invention relates to a method for determining the identity of a single nucleotide in a nucleic acid sequence, which includes the steps of: (a) conducting a nucleic acid polymerase reaction in the presence of at least one terminal phosphate-labeled nucleotide of current invention, which reaction results in the production of labeled polyphosphate; (b) detecting the presence of labeled polyphosphate; and (d) identifying the nucleoside incorporated.

The present invention further includes a nucleic acid detection kit wherein the kit includes:

(a) at least one or more terminal-phosphate-labeled nucleotide according to Formula I below:

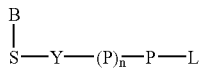

wherein P=phosphate (PO$_3$) and derivatives thereof, n is 3 or greater; Y is an oxygen or sulfur atom; B is a nitrogen-containing heterocyclic base; S is an acyclic moiety, carbocyclic moiety or sugar moiety; L is a label containing a hydroxyl group, a sulfhydryl group, a haloalkyl or an amino group suitable for forming a phosphate ester, a thioester, an alkyl phosphonate or a phosphoramidate linkage at the terminal phosphate of a natural or modified nucleotide; P-L is a phosphorylated label which preferably becomes independently detectable when the phosphate is removed.

(b) at least one of DNA polymerase, RNA polymerase, or reverse transcriptase; and (c) phosphatase or, phosphate or polyphosphate transferring enzyme.

BRIEF DESCRIPTION OF DRAWINGS

FIG. 4 presents synthetic oligonucleotide sequences.

DETAILED DESCRIPTION OF INVENTION

Figure 1:
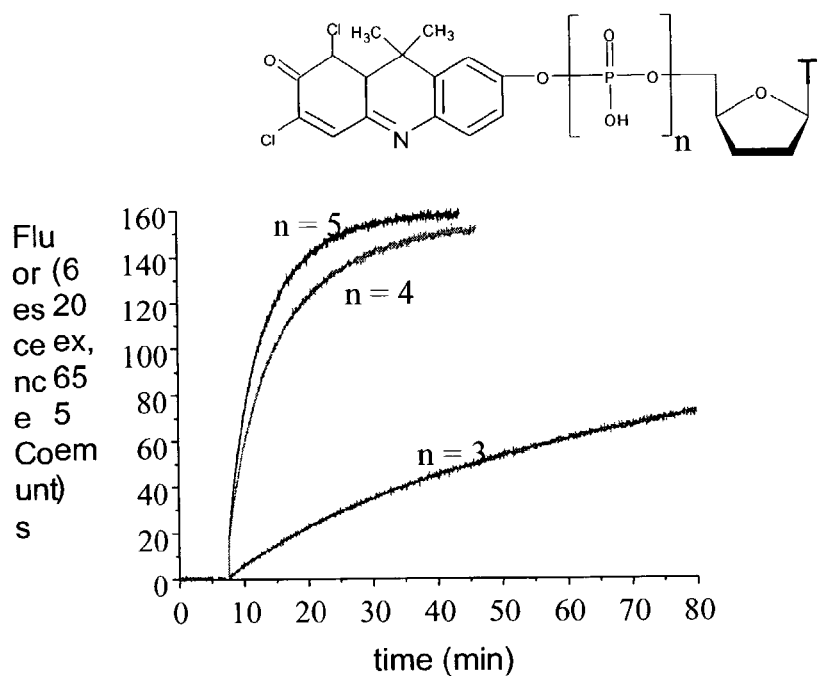
FIG. 1 presents a comparison of the rates of incorporation of a terminal phosphate labeled nucleoside tri-, tetra- and penta-phosphate analog by a DNA polymerase as measured by the release of free dye after phosphatase treatment.

The term "nucleoside" as defined herein is a compound including a purine deazapurine, pyrimidine or modified base linked to a sugar or a sugar substitute, such as a carbocyclic or acyclic moiety, at the 1' position or equivalent position and includes 2'-deoxy and 2'-hydroxyl, and 2',3'-dideoxy forms as well as other substitutions.

The term "nucleotide" as used herein refers to a phosphate ester of a nucleoside, wherein the esterification site typically corresponds to the hydroxyl group attached to the C-5 position of the pentose sugar.

The term "oligonucleotide" includes linear oligomers of nucleotides or derivatives thereof, including deoxyribonucleosides, ribonucleosides, and the like. Throughout the specification, whenever an oligonucleotide is represented by a sequence of letters, the nucleotides are in the 5'→3' order from left to right where A denotes deoxyadenosine, C denotes deoxycytidine, G denotes deoxyguanosine, and T denotes thymidine, unless noted otherwise.

The term "primer" refers to a linear oligonucleotide that anneals in a specific way to a unique nucleic acid sequence and allows for amplification of that unique sequence.

The phrase "target nucleic acid sequence" and the like refers to a nucleic acid whose sequence identity, or ordering or location of nucleosides is determined by one or more of the methods of the present invention.

The present invention provides new compositions of matter in the form of terminal phosphate labeled nucleoside polyphosphates of formula 1,

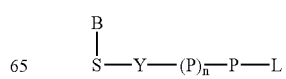

wherein P=phosphate (PO₃) and derivatives thereof, n is 3 or greater; Y is an oxygen or sulfur atom; B is a nitrogen-containing heterocyclic base; S is an acyclic moiety, carbocyclic moiety or sugar moiety; L is a fluorescent, a chemiluminescent, a colored, or an electrochemical label containing a hydroxyl group, a sulfhydryl group, a haloalkyl group or an amino group suitable for forming a phosphate ester, a thioester, an alkyl phosphonate or a phosphoramidate linkage at the terminal phosphate of a natural or modified nucleotide; Label is detectable with or without separation, P-L is a phosphorylated label which preferably becomes independently detectable when the phosphate is removed. It should be noted the alkyl phosphonate linkage is very difficult to cleave and in this case label-phosphate or label-polyphosphate is detected.

In certain embodiments, the sugar moiety in Formula I may be selected from the following: ribosyl, 2'-deoxyribosyl, 3'-deoxyribosyl, 2',3'-didehydrodideoxyribosyl, 2',3'-dideoxyribosyl, 2'- or 3'-alkoxyribosyl, 2'- or 3'-aminoribosyl, 2'- or 3'-fluororibosyl, 2'- or 3'-mercaptoribosyl, 2'- or 3'-alkylthioribosyl, acyclic, carbocyclic and other modified sugars.

For purposes of the methods of the present invention, useful carbocyclic moieties have been described by Ferraro, M. and Gotor, V. in Chem Rev. 2000, volume 100, 4319–48. Suitable sugar moieties are described by Joeng, L. S. et al., in J Med. Chem. 1993, vol. 356, 2627–38; by Kim H. O. et al., in J Med. Chem. 193, vol. 36, 30–7; and by Eschenmosser A., in Science 1999, vol. 284, 2118–2124. Moreover, useful acyclic moieties have been described by Martinez, C. I., et al., in Nucleic Acids Research 1999, vol. 27, 1271–1274; by Martinez, C. I., et al., in Bioorganic & Medicinal Chemistry Letters 1997, vol. 7, 3013–3016; and in U.S. Pat. No. 5,558,91 to Trainer, G. L. Structures for these moieties are shown below, where for all moieties R may be H, OH, NHR, F, N₃, SH, SR, OR lower alkyl and aryl; for the sugar moieties X and Y are independently O, S, or NH; and for the acyclic moieties, X=O, S, NH, NR.

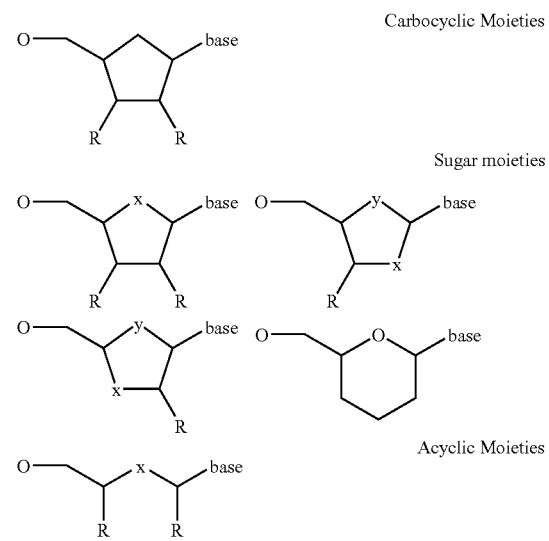

Moreover, in Formula I, the base may include uracil, thymine, cytosine, 5-methylcytosine, guanine, 7-deazaguanine, hypoxanthine, 7-deazahypoxanthine, adenine, 7-deazaadenine, 2,6-diaminopurine or analogs thereof.

The label attached at the terminal-phosphate position in the terminal-phosphate-labeled nucleotide may be selected from the group consisting of chemiluminescent compounds, fluorogenic dyes, chromogenic dyes, and electrochemical tags. This would allow the detectable species to be detectable by the presence of any one of color, fluorescence emission, chemiluminescene, electrochemical detection or a combination thereof.

Examples of labels that may be attached to the terminal phosphate group either directly or through linkers are give in Tables 1–2 below and some examples of terminal phosphate labeled nucleoside polyphosphates are shown in Table 3.

TABLE 1

Examples of detectable label moieties that become independently detectable after removal of phosphate residues

| | |
|---|---|
| 9H-(1,3-dichloro-9,9-dimethyl-7-hydroxyacridin-2-one) | 9H-(9,9-dimethyl-7-hydroxyacridin-2-one) |
| 9H-(1,3-dibromo-9,9-dimethyl-7-hydroxyacridin-2-one) | Resorufin |
| Umbelliferone (7-hydroxycoumarin) | 4-Methylumbelliferone |
| 4-Trifluoromethylumbelliferone | 3-Cyanoumbelliferone |
| 3-Phenylumbelliferone | 3,4-Dimethylumbelliferone |
| 3-Acetylumbelliferone | 6-Methoxyumbelliferone |
| SNAFL ™ | Fluorescein ethyl ether |
| Naphthofluorescein | Naphthofluorescein ethyl ether |
| SNARF ™ | Rhodol green ™ |
| meso-Hydroxymonocarbocyanine | meso-hydroxytricarbocyanine |
| meso-hydroxydicarbocyanine | bis-(1,3-dibutylbarbituric acid)pentamethine oxonol |
| 1-Ethyl-2-(naphthyl-1-vinylene)-3,3-dimethyl-indolinium salt | 2-Hydroxy-5'-chloro-phenyl-4-(3H)-6-chloro-quinazolone |
| Trifluoroacetyl-R110 | Acetyl-R110 |
| 8-Hydroxy-2H-dibenz(b,f)azepin-2-one | 8-hydroxy-11,11-dimethyl-11H-dibenz(b,e)(1,4)oxazepin-2-one |
| 2-hydroxy-11,11-dimethyl-11H-dibenz(b,e)(1,4)oxazepin-8-one | Hydroxypyrene |

TABLE 2

Examples of detectable moieties that are detectable even when attached to the nucleoside polyphosphate

| | |
|---|---|
| Rhodamine green carboxylic acid | Carboxy-fluorescein |
| Pyrene | Dansyl |
| Bodipy | Dimethylamino-coumarin carboxylic acid |
| Eosin-5-isothiocyanate | Methoxycoumarin carboxylic acid |

TABLE 2-continued

Examples of detectable moieties that are detectable even when attached to the nucleoside polyphosphate

| | |
|---|---|
| Texas Red | Oregon Green ™ 488 carboxylic acid |
| ROX | TAMRA |
| Anthracene-isothiocyanate | Cy3 |
| Cy3.5 | Cy5 |
| Cy5.5 | Anilinonaphthalene-sulfonic acid |

TABLE 3

Some examples of Labeled Nucleoside Polyphosphates

Adenosine-5'-(δ-7-(9H-(1,3-dichloro-9,9-dimethylacridin-2-one)))tetraphosphate or A4P-DDAO
Guanosine-5'-(δ-7-(9H-(1,3-dichloro-9,9-dimethylacridin-2-one)))tetraphosphate or G4P-DDAO
Cytidine-5'-(δ-7-(9H-(1,3-dichloro-9,9-dimethylacridin-2-one)))tetraphosphate or C4P-DDAO
Thymidine-5'-(δ-7-(9H-(1,3-dichloro-9,9-dimethylacridin-2-one)))tetraphosphate orT4P-DDAO
Uridine-5'-(δ-7-(9H-(1,3-dichloro-9,9-dimethylacridin-2-one)))tetraphosphate or U4P-DDAO
2'-Deoxyadenosine-5'-(δ-7-(9H-(1,3-dichloro-9,9-dimethylacridin-2-one)))tetraphosphate or dA4P-DDAO
2'-Deoxyguanosine-5'-(δ-7-(9H-(1,3-dichloro-9,9-dimethylacridin-2-one)))tetraphosphate or dG4P-DDAO
2'-Deoxycytidine-5'-(δ-7-(9H-(1,3-dichloro-9,9-dimethylacridin-2-one)))tetraphosphate or dC4P-DDAO
2'-Deoxythymidine-5'-(δ-7-(9H-(1,3-dichloro-9,9-dimethylacridin-2-one)))tetraphosphate or dT4P-DDAO
2'-Deoxyuridine-5'-(δ-7-(9H-(1,3-dichloro-9,9-dimethylacridin-2-one)))tetraphosphate or dU4P-DDAO
2',3'-Dideoxyadenosine-5'-(δ-7-(9H-(1,3-dichloro-9,9-dimethylacridin-2-one)))tetraphosphate or ddA4P-DDAO
2',3'-Dideoxyguanosine-5'-(δ-7-(9H-(1,3-dichloro-9,9-dimethylacridin-2-one)))tetraphosphate or ddG4P-DDAO
2',3'-Dideoxycytidine-5'-(δ-7-(9H-(1,3-dichloro-9,9-dimethylacridin-2-one)))tetraphosphate or ddC4P-DDAO
2',3'-Dideoxythymidine-5'-(δ-7-(9H-(1,3-dichloro-9,9-dimethylacridin-2-one)))tetraphosphate or ddT4P-DDAO
2',3'-Dideoxyuridine-5'-(δ-7-(9H-(1,3-dichloro-9,9-dimethylacridin-2-one)))tetraphosphate or ddU4P-DDAO
3'-Deoxyadenosine-5'-(δ-7-(9H-(1,3-dichloro-9,9-dimethylacridin-2-one)))tetraphosphate or 3'-dA4P-DDAO
3'-Deoxyguanosine-5'-(δ-7-(9H-(1,3-dichloro-9,9-dimethylacridin-2-one)))tetraphosphate or 3'-dG4P-DDAO
3'-Deoxycytidine-5'-(δ-7-(9H-(1,3-dichloro-9,9-dimethylacridin-2-one)))tetraphosphate or 3'-dC4P-DDAO
3'-Deoxythymidine-5'-(δ-7-(9H-(1,3-dichloro-9,9-dimethylacridin-2-one)))tetraphosphate or 3'-dT4P-DDAO
3'-Deoxyuridine-5'-(δ-7-(9H-(1,3-dichloro-9,9-dimethylacridin-2-one)))tetraphosphate or 3'-dU4P-DDAO
Adenosine-5'-(δ-7-(9H-(1,3-dichloro-9,9-dimethylacridin-2-one)))pentaphosphate or A5P-DDAO
Guanosine-5'-(δ-7-(9H-(1,3-dichloro-9,9-dimethylacridin-2-one)))tetraphosphate or G5P-DDAO
Cytidine-5'-(δ-7-(9H-(1,3-dichloro-9,9-dimethylacridin-2-one)))tetraphosphate or C5P-DDAO
Thymidine-5'-(δ-7-(9H-(1,3-dichloro-9,9-dimethylacridin-2-one)))tetraphosphate orT5P-DDAO
Uridine-5'-(δ-7-(9H-(1,3-dichloro-9,9-dimethylacridin-2-one)))tetraphosphate or U5P-DDAO
2'-Deoxyadenosine-5'-(δ-7-(9H-(1,3-dichloro-9,9-dimethylacridin-2-one)))pentaphosphate or dA5P-DDAO
2'-Deoxyguanosine-5'-(ε-7-(9H-(1,3-dichloro-9,9-dimethylacridin-2-one)))pentaphosphate or dG5P-DDAO
2'-Deoxycytidine-5'-(ε-7-(9H-(1,3-dichloro-9,9-dimethylacridin-2-one)))pentaphosphate or dC5P-DDAO
2'-Deoxythymidine-5'-(ε-7-(9H-(1,3-dichloro-9,9-dimethylacridin-2-one)))pentaphosphate or dT5P-DDAO
2'-Deoxyuridine-5'-(ε-7-(9H-(1,3-dichloro-9,9-dimethylacridin-2-one)))pentaphosphate or dU5P-DDAO
2',3'-Dideoxyadenosine-5'-(ε-7-(9H-(1,3-dichloro-9,9-dimethylacridin-2-one)))pentaphosphate or ddA5P-DDAO
2',3'-Dideoxyguanosine-5'-(ε-7-(9H-(1,3-dichloro-9,9-dimethylacridin-2-one)))pentaphosphate or ddG5P-DDAO
2',3'-Dideoxycytidine-5'-(ε-7-(9H-(1,3-dichloro-9,9-dimethylacridin-2-one)))pentaphosphate or ddC5P-DDAO
2',3'-Dideoxythymidine-5'-(ε-7-(9H-(1,3-dichloro-9,9-dimethylacridin-2-one)))pentaphosphate or ddT5P-DDAO
2',3'-Dideoxyuridine-5'-(ε-7-(9H-(1,3-dichloro-9,9-dimethylacridin-2-one)))pentaphosphate or ddU5P-DDAO TABLE 3-continued Some examples of Labeled Nucleoside Polyphosphates 3'-Deoxyadenosine-5'-(ε-7-(9H-(1,3-dichloro-9,9-dimethylacridin-2-one)))pentaphosphate or 3'-dA5P-DDAO
3'-Deoxyguanosine-5'-(ε-7-(9H-(1,3-dichloro-9,9-dimethylacridin-2-one)))pentaphosphate or 3'-dG5P-DDAO
3'-Deoxycytidine-5'-(ε-7-(9H-(1,3-dichloro-9,9-dimethylacridin-2-one)))pentaphosphate or 3'-dC5P-DDAO
3'-Deoxythymidine-5'-(ε-7-(9H-(1,3-dichloro-9,9-dimethylacridin-2-one)))pentaphosphate or 3'-dT5P-DDAO
3'-Deoxyuridine-5'-(ε-7-(9H-(1,3-dichloro-9,9-dimethylacridin-2-one)))pentaphosphate or 3'-dU5P-DDAO
Adenosine-5'-(ξ-7-(9H-(1,3-dichloro-9,9-dimethylacridin-2-one)))hexaphosphate or A6P-DDAO
Guanosine-5'-(ξ-7-(9H-(1,3-dichloro-9,9-dimethylacridin-2-one)))hexaphosphate or G6P-DDAO
Cytidine-5'-(ξ-7-(9H-(1,3-dichloro-9,9-dimethylacridin-2-one)))hexaphosphate or C6P-DDAO
Thymidine-5'-(ξ-7-(9H-(1,3-dichloro-9,9-dimethylacridin-2-one)))hexaphosphate or T6P-DDAO
Uridine-5'-(ξ-7-(9H-(1,3-dichloro-9,9-dimethylacridin-2-one)))hexaphosphate or U6P-DDAO
2'-Deoxyadenosine-5'-(ξ-7-(9H-(1,3-dichloro-9,9-dimethylacridin-2-one)))hexaphosphate or dA6P-DDAO
2'-Deoxyguanosine-5'-(ξ-7-(9H-(1,3-dichloro-9,9-dimethylacridin-2-one)))hexaphosphate or dG6P-DDAO
2'-Deoxycytidine-5'-(ξ-7-(9H-(1,3-dichloro-9,9-dimethylacridin-2-one)))hexaphosphate or dC6P-DDAO
2'-Deoxythymidine-5'-(ξ-7-(9H-(1,3-dichloro-9,9-dimethylacridin-2-one)))hexaphosphate or dT6P-DDAO
2'-Deoxyuridine-5'-(ξ-7-(9H-(1,3-dichloro-9,9-dimethylacridin-2-one)))hexaphosphate or dU6P-DDAO
2',3'-Dideoxyadenosine-5'-(ξ-7-(9H-(1,3-dichloro-9,9-dimethylacridin-2-one)))hexaphosphate or ddA6P-DDAO
2',3'-Dideoxyguanosine-5'-(ξ-7-(9H-(1,3-dichloro-9,9-dimethylacridin-2-one)))hexaphosphate or ddG6P-DDAO
2',3'-Dideoxycytidine-5'-(ξ-7-(9H-(1,3-dichloro-9,9-dimethylacridin-2-one)))hexaphosphate or ddC6P-DDAO
2',3'-Dideoxythymidine-5'-(ξ-7-(9H-(1,3-dichloro-9,9-dimethylacridin-2-one)))hexaphosphate or ddT6P-DDAO
2',3'-Dideoxyuridine-5'-(ξ-7-(9H-(1,3-dichloro-9,9-dimethylacridin-2-one)))hexaphosphate or ddU6P-DDAO
3'-Deoxyadenosine-5'-(ξ-7-(9H-(1,3-dichloro-9,9-dimethylacridin-2-one)))hexaphosphate or 3'-dA6P-DDAO
3'-Deoxyguanosine-5'-(ξ-7-(9H-(1,3-dichloro-9,9-dimethylacridin-2-one)))hexaphosphate or 3'-dG6P-DDAO
3'-Deoxycytidine-5'-(ξ-7-(9H-(1,3-dichloro-9,9-dimethylacridin-2-one)))hexaphosphate or 3'-dC6P-DDAO
3'-Deoxythymidine-5'-(ξ-7-(9H-(1,3-dichloro-9,9-dimethylacridin-2-one)))hexaphosphate or 3'-dT6P-DDAO
3'-Deoxyuridine-5'-(ξ-7-(9H-(1,3-dichloro-9,9-dimethylacridin-2-one)))hexaphosphate or 3'-dU6P-DDAO
Adenosine-5'-(δ-7-umbelliferone)tetraphosphate or A4P-Umb
Guanosine-5'-(δ-7-umbelliferone))tetraphosphate or G4P-Umb
Cytidine-5'-(δ-7-umbelliferone)tetraphosphate or C4P-Umb
Thymidine-5'-(δ-7-umbelliferone)tetraphosphate or T4P-Umb
Uridine-5'-(δ-7-umbelliferone)tetraphosphate or U4P-Umb
2'-Deoxyadenosine-5'-(δ-7-umbelliferone)tetraphosphate or dA4P-Umb
2'-Deoxyguanosine-5'-(δ-7-umbelliferone)tetraphosphate or dG4P-Umb
2'-Deoxycytidine-5'-(δ-7-umbelliferone)tetraphosphate or dC4P-Umb
2'-Deoxythymidine-5'-(δ-7-umbelliferone)tetraphosphate or dT4P-Umb
2'-Deoxyuridine-5'-(δ-7-umbelliferone)tetraphosphate or dU4P-Umb
2',3'-Dideoxyadenosine-5'-(δ-7-umbelliferone)tetraphosphate or ddA4P-Umb
2',3'-Dideoxyguanosine-5'-(δ-7-umbelliferone)tetraphosphate or ddG4P-Umb
2',3'-Dideoxycytidine-5'-(δ-7-umbelliferone)tetraphosphate or ddC4P-Umb
2',3'-Dideoxythymidine-5'-(δ-7-umbelliferone)tetraphosphate or ddT4P-Umb
2',3'-Dideoxyuridine-5'-(δ-7-umbelliferone)tetraphosphate or ddU4P-Umb
3'-Deoxyadenosine-5'-(δ-7-umbelliferone)tetraphosphate or 3'-dA4P-Umb
3'-Deoxyguanosine-5'-(δ-7-umbelliferone)tetraphosphate or 3'-dG4P-Umb
3'-Deoxycytidine-5'-(δ-7-umbelliferone)tetraphosphate or 3'-dC4P-Umb
3'-Deoxythymidine-5'-(δ-7-umbelliferone)tetraphosphate or 3'-dT4P-Umb
3'-Deoxyuridine-5'-(δ-7-umbelliferone)tetraphosphate or 3'-dU4P-Umb
Adenosine-5'-(ε-7-umbelliferone)pentaphosphate or A5P-Umb
Guanosine-5'-(ε-7-umbelliferone)pentaphosphate or G5P-Umb
Cytidine-5'-(ε-7-umbelliferone)pentaphosphate or C5P-Umb
Thymidine-5'-(ε-7-umbelliferone)pentaphosphate or T5P-Umb
Uridine-5'-(ε-7-umbelliferone)pentaphosphate or U5P-Umb
2'-Deoxyadenosine-5'-(ε-7-umbelliferone)pentaphosphate or dA5P-Umb
2'-Deoxyguanosine-5'-(ε-7-umbelliferone)pentaphosphate or dG5P-Umb
2'-Deoxycytidine-5'-(ε-7-umbelliferone)pentaphosphate or dC5P-Umb TABLE 3-continued Some examples of Labeled Nucleoside Polyphosphates 2'-Deoxythymidine-5'-(ε-7-umbelliferone)pentaphosphate or dT5P-Umb
2'-Deoxyuridine-5'-(ε-7-umbelliferone)pentaphosphate or dU5P-Umb
2',3'-Dideoxyadenosine-5'-(ε-7-umbelliferone)pentaphosphate or ddA5P-Umb
2',3'-Dideoxyguanosine-5'-(ε-7-umbelliferone)pentaphosphate or ddG5P-Umb
2',3'-Dideoxycytidine-5'-(ε-7-umbelliferone)pentaphosphate or ddC5P-Umb
2',3'-Dideoxythymidine-5'-(ε-7-umbelliferone)pentaphosphate or ddT5P-Umb
2',3'-Dideoxyuridine-5'-(ε-7-umbelliferone)pentaphosphate or ddU5P-Umb
3'-Deoxyadenosine-5'-(ε-7-umbelliferone)pentaphosphate or 3'-dA5P-Umb
3'-Deoxyguanosine-5'-(ε-7-umbelliferone)pentaphosphate or 3'-dG5P-Umb
3'-Deoxycytidine-5'-(ε-7-umbelliferone)pentaphosphate or 3'-dC5P-Umb
3'-Deoxythymidine-5'-(ε-7-umbelliferone)pentaphosphate or 3'-dT5P-Umb
3'-Deoxyuridine-5'-(ε-7-umbelliferone)pentaphosphate or 3'-dU5P-Umb
Adenosine-5'-(ξ-7-umbelliferone)hexaphosphate or A6P-Umb
Guanosine-5'-(ξ-7-umbelliferone)hexaphosphate or G6P-Umb
Cytidine-5'-(ξ-7-umbelliferone)hexaphosphate or C6P-Umb
Thymidine-5'-(ξ-7-umbelliferone)hexaphosphate or T6P-Umb
Uridine-5'-(ξ-7-umbelliferone)hexaphosphate or U6P-Umb
2'-Deoxyadenosine-5'-(ξ-7-umbelliferone)hexaphosphate or dA6P-Umb
2'-Deoxyguanosine-5'-(ξ-7-umbelliferone)hexaphosphate or dG6P-Umb
2'-Deoxycytidine-5'-(ξ-7-umbelliferone)hexaphosphate or dC6P-Umb
2'-Deoxythymidine-5'-(ξ-7-umbelliferone)hexaphosphate or dT6P-Umb
2'-Deoxyuridine-5'-(ξ-7-umbelliferone)hexaphosphate or dU6P-Umb
2',3'-Dideoxyadenosine-5'-(ξ-7-umbelliferone)hexaphosphate or ddA6P-Umb
2',3'-Dideoxyguanosine-5'-(ξ-7-umbelliferone)hexaphosphate or ddG6P-Umb
2',3'-Dideoxycytidine-5'-(ξ-7-umbelliferone)hexaphosphate or ddC6P-Umb
2',3'-Dideoxythymidine-5'-(ξ-7-umbelliferone)hexaphosphate or ddT6P-Umb
2',3'-Dideoxyuridine-5'-(ξ-7-umbelliferone)hexaphosphate or ddU6P-Umb
3'-Deoxyadenosine-5'-(ξ-7-umbelliferone)hexaphosphate or 3'-dA6P-Umb
3'-Deoxyguanosine-5'-(ξ-7-umbelliferone)hexaphosphate or 3'-dG6P-Umb
3'-Deoxycytidine-5'-(ξ-7-umbelliferone)hexaphosphate or 3'-dC6P-Umb
3'-Deoxythymidine-5'-(ξ-7-umbelliferone)hexaphosphate or 3'-dT6P-Umb
3'-Deoxyuridine-5'-(ξ-7-umbelliferone)hexaphosphate or 3'-dU6P-Umb
Adenosine-5'-(δ-7-(4-methylumbelliferone))tetraphosphate or A4P-MeUmb
Guanosine-5'-(δ-7-(4-methylumbelliferone))))tetraphosphate or G4P-MeUmb
Cytidine-5'-(δ-7-(4-methylumbelliferone))tetraphosphate or C4P-MeUmb
Thymidine-5'-(δ-7-(4-methylumbelliferone))tetraphosphate or T4P-MeUmb
Uridine-5'-(δ-7-(4-methylumbelliferone))tetraphosphate or U4P-MeUmb
2'-Deoxyadenosine-5'-(δ-7-(4-methylumbelliferone))tetraphosphate or dA4P-MeUmb
2'-Deoxyguanosine-5'-(δ-7-(4-methylumbelliferone))tetraphosphate or dG4P-MeUmb
2'-Deoxycytidine-5'-(δ-7-(4-methylumbelliferone))tetraphosphate or dC4P-MeUmb
2'-Deoxythymidine-5'-(δ-7-(4-methylumbelliferone))tetraphosphate or dT4P-MeUmb
2'-Deoxyuridine-5'-(δ-7-(4-methylumbelliferone))tetraphosphate or dU4P-MeUmb
2',3'-Dideoxyadenosine-5'-(δ-7-(4-methylumbelliferone))tetraphosphate or ddA4P-MeUmb
2',3'-Dideoxyguanosine-5'-(δ-7-(4-methylumbelliferone))tetraphosphate or ddG4P-MeUmb
2',3'-Dideoxycytidine-5'-(δ-7-(4-methylumbelliferone))tetraphosphate or ddC4P-MeUmb
2',3'-Dideoxythymidine-5'-(δ-7-(4-methylumbelliferone))tetraphosphate or ddT4P-MeUmb
2',3'-Dideoxyuridine-5'-(δ-7-(4-methylumbelliferone))tetraphosphate or ddU4P-MeUmb
3'-Deoxyadenosine-5'-(δ-7-(4-methylumbelliferone))tetraphosphate or 3'-dA4P-MeUmb
3'-Deoxyguanosine-5'-(δ-7-(4-methylumbelliferone))tetraphosphate or 3'-dG4P-MeUmb
3'-Deoxycytidine-5'-(δ-7-(4-methylumbelliferone))tetraphosphate or 3'-dC4P-MeUmb
3'-Deoxythymidine-5'-(δ-7-(4-methylumbelliferone))tetraphosphate or 3'-dT4P-MeUmb
3'-Deoxyuridine-5'-(δ-7-(4-methylumbelliferone))tetraphosphate or 3'-dU4P-MeUmb
Adenosine-5'-(ε-7-(4-methylumbelliferone))pentaphosphate or A5P-MeUmb
Guanosine-5'-(ε-7-(4-methylumbelliferone))pentaphosphate or G5P-MeUmb
Cytidine-5'-(ε-7-(4-methylumbelliferone))pentaphosphate or C5P-MeUmb
Thymidine-5'-(ε-7-(4-methylumbelliferone))pentaphosphate or T5P-MeUmb
Uridine-5'-(ε-7-(4-methylumbelliferone))pentaphosphate or U5P-MeUmb
2'-Deoxyadenosine-5'-(ε-7-(4-methylumbelliferone))pentaphosphate or dA5P-MeUmb
2'-Deoxyguanosine-5'-(ε-7-(4-methylumbelliferone))pentaphosphate or dG5P-MeUmb
2'-Deoxycytidine-5'-(ε-7-(4-methylumbelliferone))pentaphosphate or dC5P-MeUmb
2'-Deoxythymidine-5'-(ε-7-(4-methylumbelliferone))pentaphosphate or dT5P-MeUmb
2'-Deoxyuridine-5'-(ε-7-(4-methylumbelliferone))pentaphosphate or dU5P-MeUmb
2',3'-Dideoxyadenosine-5'-(ε-7-(4-methylumbelliferone))pentaphosphate or ddA5P-MeUmb
2',3'-Dideoxyguanosine-5'-(ε-7-(4-methylumbelliferone))pentaphosphate or ddG5P-MeUmb
2',3'-Dideoxycytidine-5'-(ε-7-(4-methylumbelliferone))pentaphosphate or ddC5P-MeUmb
2',3'-Dideoxythymidine-5'-(ε-7-(4-methylumbelliferone))pentaphosphate or ddT5P-MeUmb
2',3'-Dideoxyuridine-5'-(ε-7-(4-methylumbelliferone))pentaphosphate or ddU5P-MeUmb
3'-Deoxyadenosine-5'-(ε-7-(4-methylumbelliferone))pentaphosphate or 3'-dA5P-MeUmb
3'-Deoxyguanosine-5'-(ε-7-(4-methylumbelliferone))pentaphosphate or 3'-dG5P-MeUmb
3'-Deoxycytidine-5'-(ε-7-(4-methylumbelliferone))pentaphosphate or 3'-dC5P-MeUmb
3'-Deoxythymidine-5'-(ε-7-(4-methylumbelliferone))pentaphosphate or 3'-dT5P-MeUmb
3'-Deoxyuridine-5'-(ε-7-(4-methylumbelliferone))pentaphosphate or 3'-dU5P-MeUmb
Adenosine-5'-(ξ-7-(4-methylumbelliferone))hexaphosphate or A6P-MeUmb
Guanosine-5'-(ξ-7-(4-methylumbelliferone))hexaphosphate or G6P-MeUmb TABLE 3-continued Some examples of Labeled Nucleoside Polyphosphates Cytidine-5'-(ξ-7-(4-methylumbelliferone))hexaphosphate or C6P-MeUmb
Thymidine-5'-(ξ,-7-(4-methylumbelliferone))hexaphosphate or T6P-MeUmb
Uridine-5'-(ξ-7-(4-methylumbelliferone))hexaphosphate or U6P-MeUmb
2'-Deoxyadenosine-5'-(ξ-7-(4-methylumbelliferone))hexaphosphate or dA6P-MeUmb
2'-Deoxyguanosine-5'-(ξ-7-(4-methylumbelliferone))hexaphosphate or dG6P-MeUmb
2'-Deoxycytidine-5'-(ξ-7-(4-methylumbelliferone))hexaphosphate or dC6P-MeUmb
2'-Deoxythymidine-5'-(ξ-7-(4-methylumbelliferone))hexaphosphate or dT6P-MeUmb
2'-Deoxyuridine-5'-(ξ-7-(4-methylumbelliferone))hexaphosphate or dU6P-MeUmb
2',3'-Dideoxyadenosine-5'-(ξ-7-(4-methylumbelliferone))hexaphosphate or ddA6P-MeUmb
2',3'-Dideoxyguanosine-5'-(ξ-7-(4-methylumbelliferone))hexaphosphate or ddG6P-MeUmb
2',3'-Dideoxycytidine-5'-(ξ-7-(4-methylumbelliferone))hexaphosphate or ddC6P-MeUmb
2',3'-Dideoxythymidine-5'-(ξ-7-(4-methylumbelliferone))hexaphosphate or ddT6P-MeUmb
2',3'-Dideoxyuridine-5'-(ξ-7-(4-methylumbelliferone))hexaphosphate or ddU6P-MeUmb
3'-Deoxyadenosine-5'-(ξ-7-(4-methylumbelliferone))hexaphosphate or 3'-dA6P-MeUmb
3'-Deoxyguanosine-5'-(ξ-7-(4-methylumbelliferone))hexaphosphate or 3'-dG6P-MeUmb
3'-Deoxycytidine-5'-(ξ-7-(4-methylumbelliferone))hexaphosphate or 3'-dC6P-MeUmb
3'-Deoxythymidine-5'-(ξ-7-(4-methylumbelliferone))hexaphosphate or 3'-dT6P-MeUmb
3'-Deoxyuridine-5'-(ξ-7-(4-methylumbelliferone))hexaphosphate or 3'-dU6P-MeUmb
Adenosine-5'-(δ-7-resorufin)tetraphosphate or A4P-RR
Guanosine-5'-(δ-7-resorufin)))tetraphosphate or G4P-RR
Cytidine-5'-(δ-7-resorufin)tetraphosphate or C4P-RR
Thymidine-5'-(δ-7-resorufin)tetraphosphate or T4P-RR
Uridine-5'-(δ-7-resorufin)tetraphosphate or U4P-RR
2'-Deoxyadenosine-5'-(δ-7-resorufin)tetraphosphate or dA4P-RR
2'-Deoxyguanosine-5'-(δ-7-resorufin)tetraphosphate or dG4P-RR
2'-Deoxycytidine-5'-(δ-7-resorufin)tetraphosphate or dC4P-RR
2'-Deoxythymidine-5'-(δ-7-resorufin)tetraphosphate or dT4P-RR
2'-Deoxyuridine-5'-(δ-7-resorufin)tetraphosphate or dU4P-RR
2',3'-Dideoxyadenosine-5'-(δ-7-resorufin)tetraphosphateorddA4P-RR
2',3'-Dideoxyguanosine-5'-(δ-7-resorufin)tetraphosphate or ddG4P-RR
2',3'-Dideoxycytidine-5'-(δ-7-resorufin)tetraphosphate or ddC4P-RR
2',3'-Dideoxythymidine-5'-(δ-7-resorufin)tetraphosphateorddT4P-RR
2',3'-Dideoxyuridine-5'-(δ-7-resorufin)tetraphosphate or ddU4P-RR
3'-Deoxyadenosine-5'-(δ-7-resorufin)tetraphosphate or 3'-dA4P-RR
3'-Deoxyguanosine-5'-(δ-7-resorufin)tetraphosphate or 3'-dG4P-RR
3'-Deoxycytidine-5'-(δ-7-resorufin)tetraphosphate or 3'-dC4P-RR
3'-Deoxythymidine-5'-(δ-7-resorufin)tetraphosphate or 3'-dT4P-RR
3'-Deoxyuridine-5'-(δ-7-resorufin)tetraphosphate or 3'-dU4P-RR
Adenosine-5'-(ε-7-resorufin)pentaphosphate or A5P-RR
Guanosine-5'-(ε-7-resorufin)pentaphosphate or G5P-RR
Cytidine-5'-(ε-7-resorufin)pentaphosphate or C5P-RR
Thymidine-5'-(ε-7-resorufin)pentaphosphate or T5P-RR
Uridine-5'-(ε-7-resorufin)pentaphosphate or U5P-RR
2'-Deoxyadenosine-5'-(ε-7-resorufin)pentaphosphate or dA5P-RR
2'-Deoxyguanosine-5'-(ε-7-resorufin)pentaphosphate or dG5P-RR
2'-Deoxycytidine-5'-(ε-7-resorufin)pentaphosphate or dC5P-RR
2'-Deoxythymidine-5'-(ε-7-resorufin)pentaphosphate or dT5P-RR
2'-Deoxyuridine-5'-(ε-7-resorufin)pentaphosphate or dU5P-RR
2',3'-Dideoxyadenosine-5'-(ε-7-resorufin)pentaphosphate or ddA5P-RR
2',3'-Dideoxyguanosine-5'-(ε-7-resorufin)pentaphosphate or ddG5P-RR
2',3'-Dideoxycytidine-5'-(ε-7-resorufin)pentaphosphate or ddC5P-RR
2',3'-Dideoxythymidine-5'-(ε-7-resorufin)pentaphosphate or ddT5P-RR
2',3'-Dideoxyuridine-5'-(ε-7-resorufin)pentaphosphate or ddU5P-RR
3'-Deoxyadenosine-5'-(ε-7-resorufin)pentaphosphate or 3'-dA5P-RR
3'-Deoxyguanosine-5'-(ε-7-resorufin)pentaphosphate or 3'-dG5P-RR
3'-Deoxycytidine-5'-(ε-7-resorufin)pentaphosphate or 3'-dC5P-RR
3'-Deoxythymidine-5'-(ε-7-resorufin)pentaphosphate or 3'-dT5P-RR
3'-Deoxyuridine-5'-(ε-7-resorufin)pentaphosphate or 3'-dU5P-RR
Adenosine-5'-(ξ-7-resorufin)hexaphosphate or A6P-RR
Guanosine-5'-(ξ-7-resorufin)hexaphosphate or G6P-RR
Cytidine-5'-(ξ-7-resorufin)hexaphosphate or C6P-RR
Thymidine-5'-(ξ-7-resorufin)hexaphosphate or T6P-RR
Uridine-5'-(ξ-7-resorufin)hexaphosphate or U6P-RR
2'-Deoxyadenosine-5'-(ξ-7-resorufin)hexaphosphate or dA6P-RR
2'-Deoxyguanosine-5'-(ξ-7-resorufin)hexaphosphate or dG6P-RR
2'-Deoxycytidine-5'-(ξ-7-resorufin)hexaphosphate or dC6P-RR
2'-Deoxythymidine-5'-(ξ-7-resorufin)hexaphosphate or dT6P-RR
2'-Deoxyuridine-5'-(ξ-7-resorufin)hexaphosphate or dU6P-RR
2',3'-Dideoxyadenosine-5'-(ξ-7-resorufin)hexaphosphate or ddA6P-RR
2',3'-Dideoxyguanosine-5'-(ξ-7-resorufin)hexaphosphate or ddG6P-RR
2',3'-Dideoxycytidine-5'-(ξ-7-resorufin)hexaphosphate or ddC6P-RR
2',3'-Dideoxythymidine-5'-(ξ-7-resorufin)hexaphosphate or ddT6P-RR

TABLE 3-continued

Some examples of Labeled Nucleoside Polyphosphates

2',3'-Dideoxyuridine-5'-(ξ-7-resorufin)hexaphosphate or ddU6P-RR
3'-Deoxyadenosine-5'-(ξ-7-resorufin)hexaphosphate or 3'-dA6P-RR
3'-Deoxyguanosine-5'-(ξ-7-resorufin)hexaphosphate or 3'-dG6P-RR
3'-Deoxycytidine-5'-(ξ-7-resorufin)hexaphosphate or 3'-dC6P-RR
3'-Deoxythymidine-5'-(ξ-7-resorufin)hexaphosphate or 3'-dT6P-RR
3'-Deoxyuridine-5'-(ξ-7-resorufin)hexaphosphate or 3'-dU6P-RR
Adenosine-5'-(δ-3'-(6'-ethoxyfluorescein))tetraphosphate or A4P-F1Et
Guanosine-5'-(δ-3'-(6'-ethoxyfluorescein))))tetraphosphate or G4P-F1Et
Cytidine-5'-(δ-3'-(6'-ethoxyfluorescein))tetraphosphate or C4P-F1Et
Thymidine-5'-(δ-3'-(6'-ethoxyfluorescein))tetraphosphate or T4P-F1Et
Uridine-5'-(δ-3'-(6'-ethoxyfluorescein))tetraphosphateorU4P-F1Et
2'-Deoxyadenosine-5'-(δ-3'-(6'-ethoxyfluorescein))tetraphosphate or d A4P-F1Et
2'-Deoxyguanosine-5'-(δ-3'-(6'-ethoxyfluorescein))tetraphosphate or dG4P-F1Et
2'-Deoxycytidine-5'-(δ-3'-(6'-ethoxyfluorescein))tetraphosphate or dC4P-F1Et
2'-Deoxythymidine-5'-(δ-3'-(6'-ethoxyfluorescein))tetraphosphate or dT4P-F1Et
2'-Deoxyuridine-5'-(δ-3'-(6'-ethoxyfluorescein))tetraphosphate or dU4P-F1Et
2',3'-Dideoxyadenosine-5'-(δ-3'-(6'-ethoxyfluorescein))tetraphosphate or ddA4P-F1Et
2',3'-Dideoxyguanosine-5'-(δ-3'-(6'-ethoxyfluorescein))tetraphosphate or ddG4P-F1Et
2',3'-Dideoxycytidine-5'-(δ-3'-(6'-ethoxyfluorescein))tetraphosphate or ddC4P-F1Et
2',3'-Dideoxythymidine-5'-(δ-3'-(6'-ethoxyfluorescein))tetraphosphate or ddT4P-F1Et
2',3'-Dideoxyuridine-5'-(δ-3'-(6'-ethoxyfluorescein))tetraphosphate or ddU4P-F1Et
3'-Deoxyadenosine-5'-(δ-3'-(6'-ethoxyfluorescein))tetraphosphate or 3'-dA4P-F1Et
3'-Deoxyguanosine-5'-(δ-3'-(6'-ethoxyfluorescein))tetraphosphate or 3'-dG4P-F1Et
3'-Deoxycytidine-5'-(δ-3'-(6'-ethoxyfluorescein))tetraphosphate or 3'-dC4P-F1Et
3'-Deoxythymidine-5'-(δ-3'-(6'-ethoxyfluorescein))tetraphosphate or 3'-dT4P-F1Et
3'-Deoxyuridine-5'-(δ-3'-(6'-ethoxyfluorescein))tetraphosphate or 3'-dU4P-F1Et
Adenosine-5'-(ε-3'-(6'-ethoxyfluorescein))pentaphosphate or A5P-F1Et
Guanosine-5'-(ε-3'-(6'-ethoxyfluorescein))pentaphosphate or G5P-F1Et
Cytidine-5'-(ε-3'-(6'-ethoxyfluorescein))pentaphosphate or C5P-F1Et
Thymidine-5'-(ε-3'-(6'-ethoxyfluorescein))pentaphosphate or T5P-F1Et
Uridine-5'-(ε-3'-(6'-ethoxyfluorescein))pentaphosphate or U5P-F1Et
2'-Deoxyadenosine-5'-(ε-3'-(6'-ethoxyfluorescein))pentaphosphate or dA5P-F1Et
2'-Deoxyguanosine-5'-(ε-3'-(6'-ethoxyfluorescein))pentaphosphate or dG5P-F1Et
2'-Deoxycytidine-5'-(ε-3'-(6'-ethoxyfluorescein))pentaphosphate or dC5P-F1Et
2'-Deoxythymidine-5'-(ε-3'-(6'-ethoxyfluorescein))pentaphosphate or dT5P-F1Et
2'-Deoxyuridine-5'-(ε-3'-(6'-ethoxyfluorescein))pentaphosphate or dU5P-F1Et
2',3'-Dideoxyadenosine-5'-(ε-3'-(6'-ethoxyfluorescein))pentaphosphate or ddA5P-F1Et
2',3'-Dideoxyguanosine-5'-(ε-3'-(6'-ethoxyfluorescein))pentaphosphate or ddG5P-F1Et
2',3'-Dideoxycytidine-5'-(ε-3'-(6'-ethoxyfluorescein))pentaphosphate or ddC5P-F1Et
2',3'-Dideoxythymidine-5'-(ε-3'-(6'-ethoxyfluorescein))pentaphosphate or ddT5P-F1Et
2',3'-Dideoxyuridine-5'-(ε-3'-(6'-ethoxyfluorescein))pentaphosphate or ddU5P-F1Et
3'-Deoxyadenosine-5'-(ε-3'-(6'-ethoxyfluorescein))pentaphosphate or 3'-d A5P-F1Et
3'-Deoxyguanosine-5'-(ε-3'-(6'-ethoxyfluorescein))pentaphosphate or 3'-dG5P-F1Et
3'-Deoxycytidine-5'-(ε-3'-(6'-ethoxyfluorescein))pentaphosphate or 3'-dC5P-F1Et
3'-Deoxythymidine-5'-(ε-3'-(6'-ethoxyfluorescein))pentaphosphate or 3'-dT5P-F1Et
3'-Deoxyuridine-5'-(ε-3'-(6'-ethoxyfluorescein))pentaphosphate or 3'-dU5P-F1Et
Adenosine-5'-(ξ-3'-(6'-ethoxyfluorescein))hexaphosphate or A6P-F1Et
Guanosine-5'-(ξ-3'-(6'-ethoxyfluorescein))hexaphosphate or G6P-F1Et
Cytidine-5'-(ξ-3'-(6'-emoxyfluorescein))hexaphosphate or C6P-F1Et
Thymidine-5'-(ξ-3'-(6'-ethoxyfluorescein))hexaphosphate or T6P-F1Et
Uridine-5'-(ξ-3'-(6'-ethoxyfluorescein))hexaphosphate or U6P-F1Et
2'-Deoxyadenosine-5'-(ξ-3'-(6'-ethoxyfluorescein))hexaphosphate or dA6P-F1Et
2'-Deoxyguanosine-5'-(ξ-3'-(6'-ethoxyfluorescein))hexaphosphate or dG6P-F1Et
2'-Deoxycytidine-5'-(ξ-3'-(6'-ethoxyfluorescein))hexaphosphate or dC6P-F1Et
2'-Deoxythymidine-5'-(ξ-3'-(6'-ethoxyfluorescein))hexaphosphate or dT6P-F1Et
2'-Deoxyuridine-5'-(ξ-3'-(6'-ethoxyfluorescein))hexaphosphate or dU6P-F1Et
2'3'-Dideoxyadenosine-5'-(ξ-3'-(6'-ethoxyfluorescein))hexaphosphate or ddA6P-F1Et
2',3'-Dideoxyguanosine-5'-(ξ-3'-(6'-ethoxyfluorescein))hexaphosphate or ddG6P-F1Et
2',3'-Dideoxycytidine-5'-(ξ-3'-(6'-ethoxyfluorescein))hexaphosphate or ddC6P-F1Et
2',3'-Dideoxythymidine-5'-(ξ-3'-(6'-ethoxyfluorescein))hexaphosphate or ddT6P-F1Et
2',3'-Dideoxyuridine-5'-(ξ,-3'-(6'-ethoxyfluorescein))hexaphosphate or ddU6P-F1Et
3'-Deoxyadenosine-5'-(ξ-3'-(6'-ethoxyfluorescein))hexaphosphate or 3'-d A6P-F1Et
3'-Deoxyguanosine-5'-(ξ-3'-(6'-ethoxyfluorescein))hexaphosphate or 3'-dG6P-F1Et
3'-Deoxycytidine-5'-(ξ-3'-(6'-ethoxyfluorescein))hexaphosphate or 3'-dC6P-F1Et
3'-Deoxythymidine-5'-(ξ-3'-(6'-ethoxyfluorescein))hexaphosphate or 3'-dT6P-F1Et
3'-Deoxyuridine-5'-(ξ-3'-(6'-ethoxyfluorescein))hexaphosphate or 3'-dU6P-F1Et Wherein the phosphorylated label in Formula I is a fluorogenic moiety, it is desirably selected from one of the following (all shown as the phosphomonester): 2-(5'-chloro-2'-phosphoryloxyphenyl)-6-chloro-4-(3H)-quinazolinone, sold under the trade name ELF 97 (Molecular Probes, Inc.), fluorescein diphosphate (tetraammonium salt), fluorescein 3'(6')-O-alkyl-6'(3')-phosphate, 9H-(1,3-dichloro-9,9-dimethylacridin-2-one-7-yl)phosphate (diammonium salt), 4-methylumbelliferyl phosphate (free acid), resorufin phosphate, 4-trifluoromethylumbelliferyl phosphate, umbelliferyl phosphate, 3-cyanoubelliferyl phosphate, 9,9-dimethylacridin-2-one-7-yl phosphate, 6,8-difluoro-4-methylumbelliferyl phosphate and derivatives thereof. Structures of these dyes are shown below:

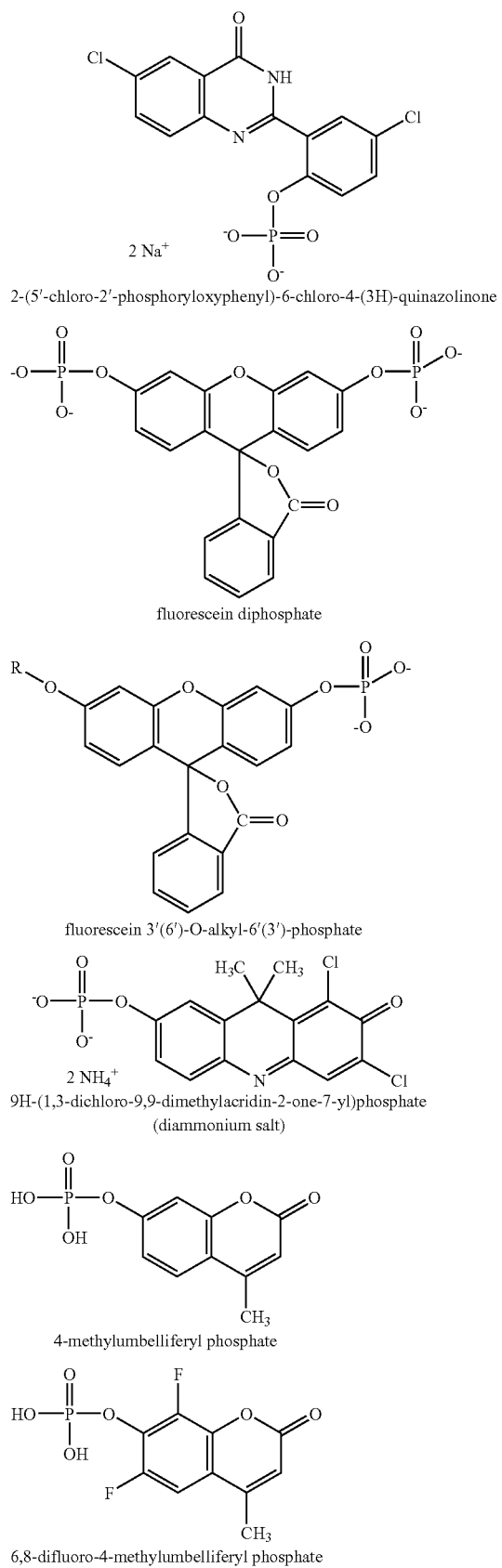
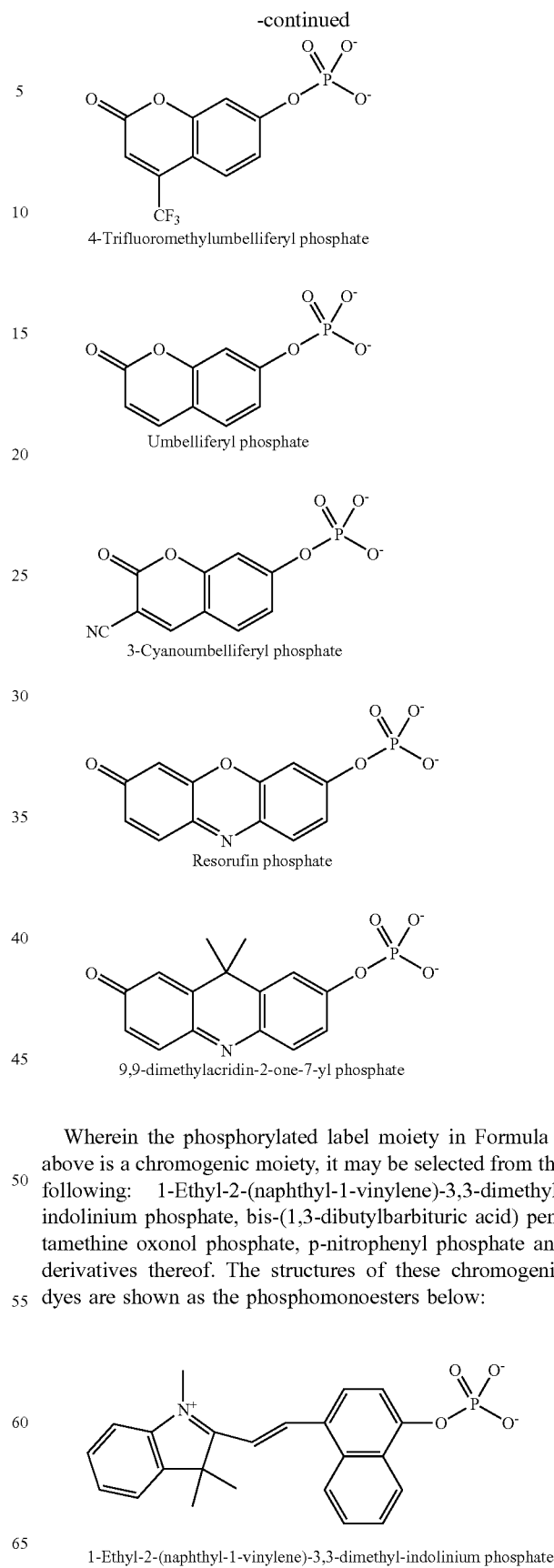

Wherein the phosphorylated label moiety in Formula I above is a chromogenic moiety, it may be selected from the following: 1-Ethyl-2-(naphthyl-1-vinylene)-3,3-dimethyl-indolinium phosphate, bis-(1,3-dibutylbarbituric acid) pentamethine oxonol phosphate, p-nitrophenyl phosphate and derivatives thereof. The structures of these chromogenic dyes are shown as the phosphomonoesters below:

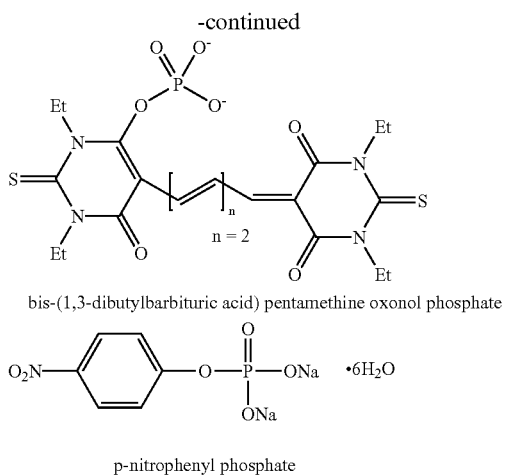

bis-(1,3-dibutylbarbituric acid) pentamethine oxonol phosphate

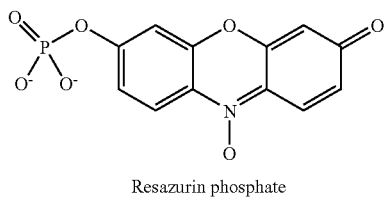

p-nitrophenyl phosphate

The moiety at the terminal-phosphate position may further be a chemiluminescent compound wherein it is desired that it is a phosphatase-activated 1,2-dioxetane compound. The 1,2-dioxetane compound may include, but is not limited to, disodium 2-chloro-5-(4-methoxyspiro[1,2-dioxetane-3,2'-(5-chloro-)tricyclo[3,3,1-1$^{3,7}$]-decan]-1-yl)-1-phenyl phosphate, sold under the trade name CDP-Star (Tropix, Inc., Bedford, Mass.), chloroadamant-2'-ylidenemethoxyphenoxy phosphorylated dioxetane, sold under the trade name CSPD (Tropix), and 3-(2'-spiroadamantane)-4-methoxy-4-(3"-phosphoryloxy)phenyl-1,2-dioxetane, sold under the trade name AMPPD (Tropix). The structures of these commercially available dioxetane compounds are disclosed in U.S. Pat. Nos. 5,582,980, 5,112,960 and 4,978,614, respectively, and are incorporated herein by reference.

The moiety at the terminal phosphate may further be any of the fluorescent, luminescent and colored dyes currently used to label biological molecules and are always "on" (Table 2). A variety of these dyes are available from commercial sources including Molecular Probes, Applied Biosystems, Atto-tec and Amersham Biosciences and can be attached to the terminal phosphate through a linker. In this case, the label may be attached through an alkyl phosphonate linkage in addition to those that are cleavable by phosphatase or phosphate transferring enzymes. It should be noted that alkylphosphonate linkage is not readily cleavable and label is expected to retain the terminal phosphate in the form of phosphonate.

The present invention provides additional compositions of matter in the form of terminal phosphate labeled nucleoside polyphosphates of formula 1 that are substrates for DNA polymerases, with more than three phosphates where the label in addition to the one's described above is a mass tag or a moiety that after phosphate removal undergoes further reaction to generate a detectable moiety. Examples of these are numerous and only a couple are shown below: Resazurin phosphate and ethyl phosphate.

Resazurin phosphate

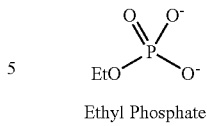

Ethyl Phosphate

For example, after cleavage of phosphate resazurin may be reacted with NAD(P)H to give fluorescent resorufin. In case of ethyl derivative, ethanol may be used by an alcohol oxidase to reduce dissolved oxygen into hydrogen peroxide. Latter can interact with other chemicals, such as acridinium esters to generate a signal. The ethanol oxidation can be further coupled to another enzymatic reaction as shown below to amplify the signal. These methods are less desirable than those where label is released directly from the corresponding phosphate, but can be useful for signal amplification or other reasons.

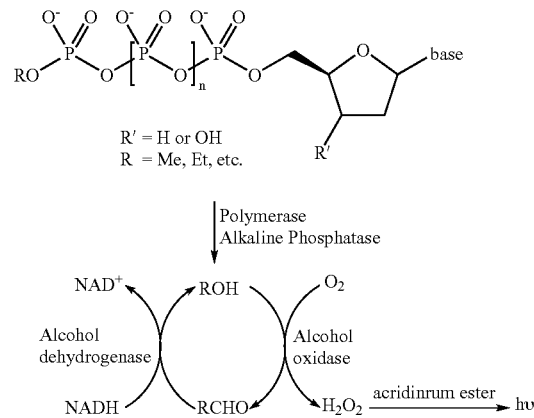

The present invention relates to methods of detecting a polynucleotide in a sample wherein a convenient assay is used for monitoring RNA or DNA synthesis via nucleic acid polymerase activity. RNA and DNA polymerases synthesize oligonucleotides via transfer of a nucleoside monophosphate from a nucleoside triphosphate (NTP) or deoxynucleoside triphosphate (dNTP) to the 3' hydroxyl of a growing oligonucleotide chain. The force which drives this reaction is the cleavage of an anhydride bond and the con-commitant formation of an inorganic pyrophosphate. The present invention utilizes the finding that structural modification of the terminal-phosphate of the nucleotide does not abolish its ability to function in the polymerase reaction. The oligonucleotide synthesis reaction involves direct changes only at the α- and β-phosphoryl groups of the nucleotide, allowing nucleotides with modifications at the terminal phosphate position to be valuable as substrates for nucleic acid polymerase reactions.

In certain embodiments, the polymerase is a DNA polymerase, such as DNA polymerase I, II, or III or DNA polymerase α, β, γ, or terminal deoxynucleotidyl transferase or telomerase. In other embodiments, suitable polymerases include, but are not limited to, a DNA dependent RNA polymerase, a primase, or an RNA dependant DNA polymerase (reverse transcriptase).

The compositions provided by this invention include a nucleoside polyphosphate, such as a deoxynucleoside polyphosphate, dideoxynucleoside polyphosphate, carbocyclic nucleoside polyphosphate, or acyclic nucleoside polyphosphate analogue with an electrochemical label, mass tag, or a colorimetric dye, chemiluminescent, or fluorescent label attached to the terminal-phosphate. When a nucleic acid polymerase uses this analogue as a substrate, an enzyme-activatable label would be present on the inorganic polyphosphate by-product of phosphoryl transfer. Cleavage of the polyphosphate product of phosphoryl transfer via phosphatase, leads to a detectable change in the label attached thereon. It is noted that while RNA and DNA polymerases are able to recognize nucleotides with modified terminal phosphoryl groups, the inventors have determined that this starting material is not a template for phosphatases. The scheme below shows the most relevant molecules in the methods of this invention; namely the terminal-phosphate-labeled nucleotide, the labeled polyphosphate by-product and the enzyme-activated label.

to phosphatase may be, for example, blocked at the terminal-phosphate by a moiety which does not lead to the production of a detectable species. The nucleic acid for detection in this particular embodiment may include RNA, a natural or synthetic oligonucleotide, mitochondrial or chromosomal DNA.

The invention further provides a method of detecting the presence of a DNA sequence including the steps of (a) conducting a DNA polymerase reaction in the presence of a terminal-phosphate labeled nucleotide, which reaction results in the production of a labeled polyphosphate; (b) permitting the labeled polyphosphate to react with a phosphatase to produce a detectable species; and (c) detecting the presence of said detectable species. The DNA sequence for detection may include DNA isolated from cells, chemically treated DNA such as bisulfite treated methylated DNA or

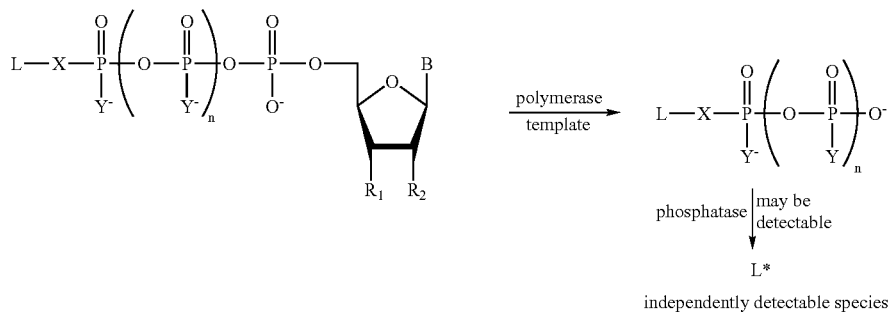

In the scheme above, n is 2 or greater, $R_1$ and $R_2$ are independently H, OH, SH, SR, OR, F, Br, Cl, I, $N_3$, NHR or $NH_2$; B is a nucleotide base or modified heterocyclic base; X is O, S, or NH; Y is O, S, or $BH_3$; and L is a phosphatase activatable label which may be a chromogenic, fluorogenic, chemiluminescent molecule, mass tag or electrochemical tag. A mass tag is a small molecular weight moiety suitable for mass spectrometry that is readily distinguishable from other components due to a difference in mass. An electrochemical tag is an easily oxidizable or reducible species. It has been discovered that when n is 2 or greater, the nucleotides are significantly better substrates for polymerases than when n is 1.

In one embodiment of the method of detecting the presence of a nucleic acid sequence provided herein, the steps include (a) conducting a nucleic acid polymerase reaction wherein the reaction includes at least one nucleotide which is substantially non-reactive to phosphatase in addition to one terminal-phosphate-labeled nucleotide wherein the polymerase reaction results in the production of labeled polyphosphate; (b) permitting the labeled polyphosphate to react with a phosphatase suitable to hydrolyze the phosphate ester and to produce a detectable species; and c) detecting the presence of a detectable species by suitable means. In this embodiment, the template used for the nucleic acid polymerase reaction may be a heteropolymeric or homopolymeric template. By terminal-phosphate-labeled nucleotide, it is meant throughout the specification that the labeled polyphosphate con-committantly released following incorporation of the nucleoside monophosphate into the growing nucleotide chain, may be reacted with the phosphatase to produce a detectable species. Other nucleotides included in the reaction which are substantially non-reactive DNA chemically or enzymatically synthesized according to methods known in the art. Such methods include PCR, and those described in DNA Structure Part A: Synthesis and Physical analysis of DNA, Lilley, D. M. J. and Dahlberg, J. E. (Eds.), Methods Enzymol., 211, Academic Press, Inc., New York (1992), which is herein incorporated by reference. The DNA sequence may further include chromosomal DNA and natural or synthetic oligonucleotides. The DNA may be either double- or single-stranded.

The methods of the invention may further include the step of including one or more additional detection reagents in the polymerase reaction. The additional detection reagent may be capable of a response that is detectably different from the detectable species. For example, the additional detection reagent may be an antibody.

Suitable nucleotides for addition as substrates in the polymerase reaction include nucleoside polyphosphates, such as including, but not limited to, deoxyribonucleoside polyphosphates, ribonucleoside polyphosphates, dideoxynucleoside polyphosphates, carbocyclic nucleoside polyphosphates and acyclic nucleoside polyphosphates and analogs thereof. Particularly desired are nucleotides containing 4, 5 or 6 phosphate groups in the polyphosphate chain, where the terminal phosphate is labeled.

It is noted that in embodiments including terminal-phosphate-labeled nucleotides having four or more phosphates in the polyphosphate chain, it is within the contemplation of the present invention that the labeled polyphosphate by-product of phosphoryl transfer may be detected without the use of phosphatase treatment. For example, it is known that natural or modified nucleoside bases, particularly guanine, can cause quenching of fluorescent markers. Therefore, in a terminal-phosphate-labeled nucleotide, the label may be partially quenched by the base. Upon incorporation of the nucleoside monophosphate, the label polyphosphate by-product may be detected due to its enhanced fluorescence. Alternatively, it is possible to physically separate the labeled polyphosphate product by chromatographic or other separation methods before identification by fluorescence, color, chemiluminescence, or electrochemical detection. in addition, mass spectrometry could be used to detect the products by mass difference.

The methods of the present invention may include conducting the polymerase reaction in the presence of at least one of DNA or RNA polymerase. Suitable nucleic acid polymerases may also include primases, telomerases, terminal deoxynucleotidyl transferases, and reverse transcriptases. A nucleic acid template may be required for the polymerase reaction to take place and may be added to the polymerase reaction solution. It is anticipated that all of the steps (a), (b) and (c) in the detection methods of the present invention could be run concurrently using a single, homogenous reaction mixture, as well as run sequentially.

It is well within the contemplation of the present invention that nucleic acid polymerase reactions may include amplification methods that utilize polymerases. Examples of such methods include polymerase chain reaction (PCR), rolling circle amplification (RCA), and nucleic acid sequence based amplification (NASBA). For e.g., wherein the target molecule is a nucleic acid polymer such as DNA, it may be detected by PCR incorporation of a gamma-phosphate labeled nucleotide base such as adenine, thymine, cytosine, guanine or other nitrogen heterocyclic bases into the DNA molecule. The polymerase chain reaction (PCR) method is described by Saiki et al in Science Vol. 239, page 487, 1988, Mullis et al in U.S. Pat. No. 4,683,195 and by Sambrook, J. et al. (Eds.), Molecular Cloning, second edition, Cold Spring Harbor Laboratory Press, Cold Spring Harbor, N.Y. (1980), Ausubel, F. M. et al. (Eds.), Current Protocols in Molecular Biology, John Wiley & Sons, Inc., NY (1999), and Wu, R. (Ed.), Recombinant DNA Methodology II, Methods in Zumulogy, Academic Press, Inc., NY, (1995). Using PCR, the target nucleic acid for detection such as DNA is amplified by placing it directly into a reaction vessel containing the PCR reagents and appropriate primers. Typically, a primer is selected which is complimentary in sequence to at least a portion of the target nucleic acid.

It is noted that nucleic acid polymerase reactions suitable for conducting step (a) of the methods of the present invention may further include various RCA methods of amplifying nucleic acid sequences. For example, those disclosed in U.S. Pat. No. 5,854,033 to Lizardi, Paul M., incorporated herein by reference, are useful. Polymerase reactions may further include the nucleic acid sequence based amplification (NASBA) wherein the system involves amplification of RNA, not DNA, and the amplification is iso-thermal, taking place at one temperature (41° C.). Amplification of target RNA by NASBA involves the coordinated activities of three enzymes: reverse transcriptase, Rnase H, and T7 RNA polymerase along with oligonucleotide primers directed toward the sample target RNA. These enzymes catalyze the exponential amplification of a target single-stranded RNA in four steps: extension, degradation, DNA synthesis and cyclic RNA amplification.

Methods of RT-PCR, RCA, and NASBA generally require that the original amount of target nucleic acid is indirectly measured by quantification of the amplification products. Amplification products are typically first separated from starting materials via electrophoresis on an agarose gel to confirm a successful amplification and are then quantified using any of the conventional detection systems for a nucleic acid such as detection of fluorescent labels, enzyme-linked detection systems, antibody-mediated label detection and detection of radioactive labels. In contrast, the present method eliminates the need to separate products of the polymerase reaction from starting materials before being able to detect these products. For example, in the present invention, a reporter molecule (fluorescent, chemiluminescent or a chromophore) or other useful molecule is attached to the nucleotide in such a way that it is undetectable under certain conditions when masked by the phosphate attachment. However, following the incorporation of the nucleotide into the growing oligonucleotide chain and phosphatase treatment of the reaction, the label is detectable under those conditions. For example, if the hydroxyl group on the side of the triple ring structure of 1,3-dichloro-9,9-dimethyl-acridine-2-one (DDAO) is attached to the terminal-phosphate position of the nucleotide, the DDAO does not fluoresce at 659 nm. Once the nucleoside monophosphate is incorporated into DNA, the other product, DDAO polyphosphate (which also does not fluoresce at 659 nm) is a substrate for phosphatase. Once de-phosphorylated to form DDAO, the dye moiety will become fluorescent at 659 nm and hence detectable. The specific analysis of the polyphosphate product can be carried out in the polymerase reaction solution, eliminating the need to separate reaction products from starting materials. This scheme allows for the detection and, optionally, quantitation of nucleic acids formed during polymerase reactions using routine instrumentation such as spectrophotometers.

In the methods described above, the polymerase reaction step may further include conducting the polymerase reaction in the presence of a phosphatase, which converts labeled polyphosphate by-product to the detectable label. As such, a convenient assay is established for detecting the presence of a nucleic acid sequence that allows for continuous monitoring of detectable species formation. This represents a homogeneous assay format in that it can be performed in a single tube.

One format of the assay methods described above may include, but is not limited to, conducting the polymerase reaction in the presence of a single type of terminal-phosphate-labeled nucleotide of current invention capable of producing a detectable species, for example terminal-phosphate-modified A4P, wherein all other nucleotides are substantially non-reactive to phosphatase, but yield non-detectable species.

In another assay format, the polymerase reaction may be conducted in the presence of more than one type of terminal-phosphate-labeled nucleotide of current invention, each type capable of producing a uniquely detectable species. For example, the assay may include a first nucleotide (e.g., adenosine polyphosphate) that is associated with a first label which when liberated enzymatically from the inorganic polyphosphate by-product of phosphoryl transfer, emits light at a first wavelength and a second nucleotide (e.g., guanosine polyphosphate) associated with a second label that emits light at a second wavelength. Desirably, the first and second wavelength emissions have substantially little or no overlap. It is within the contemplation of the present invention that multiple simultaneous assays based on nucleotide sequence information can thereafter be derived based on the particular label released from the polyphosphate.

The methods described above may further include the step of quantifying the nucleic acid sequence. In a related aspect, the detectable species may be produced in amounts substantially proportional to the amount of an amplified nucleic acid sequence. The step of quantifying the nucleic acid sequence is desired to be done by comparison of spectra produced by the detectable species with known spectra.

In one embodiment, the invention provides a method of quantifying a nucleic acid including the steps of: (a) conducting a nucleic acid polymerase reaction, the polymerase reaction including the reaction of a nucleotide which is substantially non-reactive to phosphatase in addition to at least one terminal-phosphate-labeled nucleotide of current invention, wherein the reaction results in the production of labeled polyphosphate; (b) permitting the labeled polyphosphate to react with a phosphatase or phosphate or polyphosphate transferring enzyme to produce a detectable by-product species in an amount substantially proportional to the amount of the nucleic acid to be quantified; (c) measuring the detectable species; and (d) comparing the measurements using known standards to determine the quantity of the nucleic acid. In this embodiment of the method of quantifying a nucleic acid, the nucleic acid to be quantified may be RNA. The nucleic acid may further be a natural or synthetic oligonucleotide, chromosomal DNA, or DNA.

The invention further provides a method of quantifying a DNA sequence including the steps of: (a) conducting a DNA polymerase reaction in the presence of a terminal-phosphate-labeled nucleotide of current invention wherein the reaction results in the production of labeled polyphosphate; (b) permitting the labeled polyphosphate to react with a phosphatase or phosphate or polyphosphate transferring enzyme to produce a detectable by-product species in amounts substantially proportional to the amount of the DNA sequence to be quantified; (c) measuring the detectable species; and (d) comparing measurements using known standards to determine the quantity of DNA. In this embodiment, the DNA sequence for quantification may include natural or synthetic oligonucleotides, or DNA isolated from cells including chromosomal DNA.

In each of these methods of quantifying a nucleic acid sequence described above, the polymerase reaction step may further include conducting the polymerase reaction in the presence of a phosphatase or phosphate or polyphosphate transferring enzyme. As described earlier in the specification, this would permit real-time monitoring of nucleic acid polymerase activity and hence, real-time detection of a target nucleic acid sequence for quantification.

The terminal-phosphate-labeled nucleotide useful for the methods of quantifying the nucleic acid sequence provided herein may be represented by the Formula I shown above. The enzyme-activatable label becomes detectable through the enzymatic activity of phosphatase or phosphate or polyphosphate transferring enzyme which changes the phosphate ester linkage between the label and the terminal-phosphate of a natural or modified nucleotide in such a way to produce a detectable species. The detectable species is detectable by the presence of any one of or a combination of color, fluoresence emission, chemiluminescence, mass difference or electrochemical potential. As already described above, the enzyme-activatable label may be a 1,2-dioxetane chemiluminescent compound, fluorescent dye, chromogenic dye, a mass tag or an electrochemical tag or a combination thereof. Suitable labels are the same as those described above.

As will be described in further detail in the Example Section, the present invention provides methods for determining the identity of a single nucleotide in a target nucleic acid sequence. These methods include the steps of: (a) conducting a nucleic acid polymerase reaction in the presence of at least one terminal phosphate-labeled nucleotide of current invention, which reaction results in the production of labeled polyphosphate; (b) permitting the labeled polyphosphate to react with a phosphatase or phosphate or polyphosphate transferring enzyme to produce a detectable species; (c) detecting the presence of the detectable species; and (d) identifying the nucleoside incorporated. In desired embodiments, the terminal phosphate-labeled nucleotide includes four or more phosphates in the polyphosphate chain.

Another aspect of the invention relates to a nucleic acid detection kit including:

(a) at least one or more terminal-phosphate-labeled nucleotides according to Formula I below:

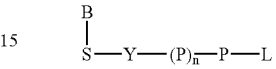

wherein P=phosphate ($PO_3$) and derivatives thereof, n is 3 or greater; Y is an oxygen or sulfur atom; B is a nitrogen-containing heterocyclic base; S is an acyclic moiety, carbocyclic moiety or sugar moiety; L is an enzyme-activatable label containing a hydroxyl group, a sulfhydryl group or an amino group suitable for forming a phosphate ester, a thioester or a phosphoramidate linkage at the terminal phosphate of a natural or modified nucleotide; P-L is a phosphorylated label which preferably becomes independently detectable when the phosphate is removed.

(b) at least one of DNA polymerase, RNA polymerase or reverse transcriptase; and (c) phosphate or polyphosphate transferring enzyme.

The sugar moiety in the terminal-phosphate-labeled nucleotide included in the kit may include, but is not limited to ribosyl, 2'-deoxyribosyl, 3'-deoxyribosyl, 2',3'-dideoxyribosyl, 2',3'-didehydrodideoxyribosyl, 2'- or 3'-alkoxyribosyl, 2'- or 3'-aminoribosyl, 2'- or 3'-fluororibosyl, 2'- or 3'-mercaptoribosyl, 2'- or 3'-alkylthioribosyl, acyclic, carbocyclic and other modified sugars.

The base may be, but is not limited to uracil, thymine, cytosine, 5-methylcytosine, guanine, 7-deazaguanine, hypoxanthine, 7-deazahypoxanthine, adenine, 7-deazaadenine and 2,6-diaminopurine and analogs thereof.

Furthermore, as described above, the enzyme-activatable label may be a 1,2-dioxetane chemiluminescent compound, fluorescent dye, chromogenic dye, a mass tag, an electrochemical tag or a combination thereof. Suitable compounds for conjugation at the terminal-phosphate position of the nucleotide are the same as those described above.

EXAMPLES

The following examples illustrate certain preferred embodiments of the illustration that are not intended to be illustrative of all embodiments.

Example 1

Preparation of γ(7-Hydroxy-3H-Phenoxazin-3-one) ddGTP (γ-Resorufin-ddGTP)

ddGTP (125 µl of 86.7 mM solution, 10.8 µmol) was coevaporated with anhydrous DMF (3×0.25 ml). To this, DCC (5 eq.) was added and the mixture was again coevaporated with anhydrous DMF (0.25 ml). Residue was taken in anhydrous DMF (1 ml) and the reaction was stirred at room temperature over a weekend. Resorufin (20 eq.) was coevaporated with anhydrous DMF (2×1 ml) and ddGTP trimetaphosphate from the above cyclization step was added, followed by 20 eq. of triethylamine. After 2 weeks, the reaction mixture was concentrated on a rotavap and the residue was extracted with water (3×2 ml) and filtered. The filtrate was purified on an Xterra RP C18 (19×100 mm) column using 0–30% acetonitrile in 0.1 M triethylammonium bicarbonate (pH 6.7) in 5 column volumes and 30–50% acetonitrile in 1 column volume. The pure fraction was concentrated on a rotavap and coevaporated with methanol (2×5 ml). The residue was dissolved in water (1.5 ml) to give a 0.5 mM solution. HPLC purity at 260 nm>98%, at 470 nm>97.5%. UV/VIS=251 and 472 nm. MS: M−1=685.10 (calc. 685.03).

UV analysis. A346 nm=0.784. Assuming an extinction coeff. of 20,000 (reported for 7-ethoxy-3-cyanocoumarin, Molecular Probes Catalog), concentration=7.84 mM. Yield=3.92 umol, 44%. Sample was repurified on C-18 column using same method as above. Sample peak was collected in 3 fractions. Fractions 2 & 3, with >98% purity at 254 nm and >99.5% purity at 340 nm, were combined. After concentration, residue was coevaporated with MeOH (2×) and water (1×). Sample was dissolved in water (1 ml) to give a 2.77 mM solution. MS: M⁻=642.98 au (calc 643.00 au), UV $\lambda_A$=263 & 346 nm The cyanocoumarin dye attached to the gamma phosphate of ddATP is fluorescent with an excitation maximum of 346 nm and an emission maximum of about

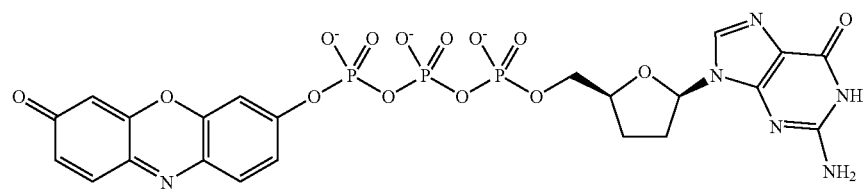

Example 2

Preparation of γ-(3-Cyanocoumarinyl)ddATP (γCNCoumarin-ddATP)

ddATP (100 μl of 89 mM solution, >96%) was coevaporated with anhydrous DMF (2×1 ml). To this DCC (9.2 mg, 411 nm. Upon hydrolysis of the phosphate ester to release the free coumarin dye, the spectrum changes with excitation maximum of about 408 nm and emission maximum of about 450 nm. This change is readily detected by simple fluorescence measurements or color change. Synthesis of gamma nucleotides has been generally described by Arzumanov, A, et al in J Biol Chem. (1996) October 4; 271(40):24389–94.

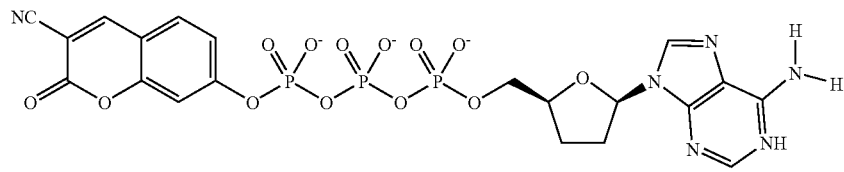

5 eq.) was added and mixture was again coevaporated with anhydrous DMF (1 ml). Residue was taken in anhydrous DMF (0.5 ml) and reaction was stirred at rt. After overnight 7-hydroxy-3-cyanocoumarin (33.3 mg, 20 eq.) and TEA (25 ul, 20 eq.), were added and mixture was stirred at RT. After 1 day, a major product (55% at 254 nm) was observed 8.1 min with another minor product at 10 min (10%). No significant change occurred after another day. Reaction mixture was concentrated on rotary evaporator and residue was extracted with 3×2 ml water and filtered. Aq solution was concentrated and purified on C-18 using 0–30% acetonitrile in 0.1M TEAB (pH 6.7) in 30 min and 30–50% acetonitrile in 10 min, flow rate 15 ml/min. Main peak was collected in 3 fractions. HPLC of the main peak (fr. 2) showed a purity of 95.6% at 254 nm and 98.1% at 335 nm. It was concentrated on rotary evaporator (at RT), coevaporated with MeOH (2×) and water (1×). Residue was dissolved in 0.5 ml water. A 5 ul sample was diluted to 1 ml for γ-(3-cyanocoumarinyl)dideoxyadenosine-5'-triphosphate (γCNCoumarin-ddATP)

Example 3

Preparation of δ-9H(1,3-dichloro-9,9-dimethylacridin-2-one-7-yl)-dideoxythymidine-5'-tetraphosphate (ddT4P-DDAO)

ddTTP (100 μl of 80 mM solution) was coevaporated with anhydrous dimethylformamide (DMF, 2×1 ml). To this dicyclohexylcarbodiimide (8.3 mg. 5 eq.) was added and the mixture was again coevaporated with anhydrous DMF (1 ml). Residue was taken in anhydrous DMF (1 ml) and reaction was stirred at room temperature overnight. HPLC showed mostly cyclized triphosphate (~82%). Reaction mixture was concentrated and residue was washed with anhydrous diethyl ether 3×. It was redissolved in anhydrous DMF and concentrated to dryness on rotavap. Residue was taken with DDAO-monophosphate, ammonium salt (5 mg, 1.5 eq.) in 200 μl anhydrous DMF and stirred at 40° C. over the weekend. HPLC showed formation of a new product with desired UV characteristics at 11.96 min. (HPLC Method: 0.30% acetonitrile in 0.1M triethylammonium acetate (pH 7) in 15 min, and 30–50% acetonitrile in 5 min, Novapak C-18 3.9×150 mm column, 1 ml/min). LCMS (ES-) also showed a major mass peak 834 for M−1 peak. Reaction mixture was concentrated and purified on Deltapak C18, 19×300 mm column using 0.1M TEAB (pH 6.7) and acetonitrile. Fraction with product was repurified by HPLC using the same method as described above. Fraction with pure product was concentrated, coevaporated with MeOH (2×) and water (1×). Residue was dissolved in water (1.2 ml) to give a 1.23 mM solution. HPCL purity as 254 nm>97.5%, at 455 nm>96%; UV $\lambda_A$=267 nm and 455 nm; MS: M−1=834.04 (calc 8.33.95).

δ-9H(1,3-dichloro-9,9-dimethylacridin-2-one-7=yl)-dideoxycytidine-5'-tetraphosphate (ddC4P-DDAO), δ-9H (1,3-dichloro-9,9-dimethylacridin-2-one-dideoxyadenosine-5'-tetraphosphate (ddA4P-DDAO) and δ-9H(1,3-dichloro-9,9-dimethylacridin-2-one-y-YL)-dideoxyguanosine-5'-tetraphosphate (ddG4P-DDAO) were synthesized and purified in a similar fashion. Analysis of these purified compounds provided the following data: ddC4P-DDAO: UV $\lambda_A$=268 nm and 454 nm; MS: M−1=819.32 (calc 818.96); ddA4P-DDAO: UV $\lambda_A$=263 nm and 457 nm; MS: M−1=843.30 (calc 842.97); ddG4P-DDAO: UV $\lambda_A$=257 nm and 457 nm; MS: M−1=859.40 (calc 858.97).

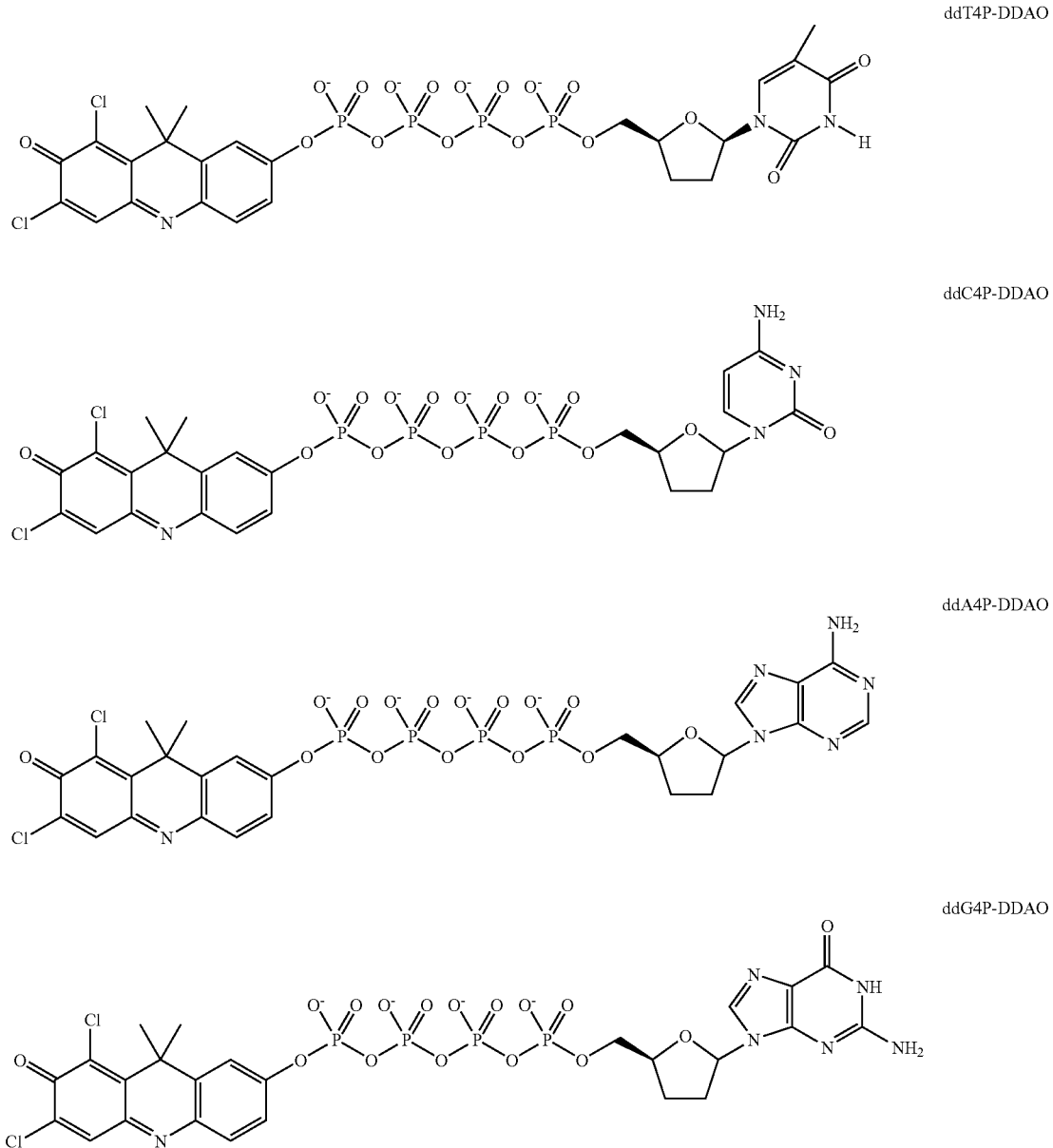

ddT4P-DDAO ddC4P-DDAO ddA4P-DDAO ddG4P-DDAO

Example 4

Preparation of δ-9H(1,3-dichloro-9,9-dimethylacridin-2-one-7-yl)-deoxythymidine-5'-tetraphosphate (dT4P-DDAO)

10 μmoles TTP TEA salt was evaporated to dryness. To the residue was added 40 μmoles tributylamine and 5 ml dry pyridine. The solution was re-evaporated to dryness. After 2 coevaporations with 3 ml dry dimethylformamide (DMF), residue was re-dissolved in 200 μl dry DMF, flushed with argon and stoppered. Using a syringe, 50 μmoles (8 mg) carbonyldiimidazole (CDI) dissolved in 100 μl dry DMF was added. The flask was stirred for 4 hr at ambient temperature.

While the above reaction was progressing, 35 mg (83 μmoles) DDAO phosphate and 166 μmoles tributylamine were dissolved in dry DMF. The DDAO phosphate was evaporated to dryness followed by 3 coevaporations with dry DMF. Residue was dissolved in 300 μl dry DMF.

After the 4 hr reaction time, 3.2 μl anhydrous methanol was added to the TTP-CDI reaction. The reaction was stirred 30 minutes. To this mixture, DDAO phosphate solution was added and mixture was stirred at ambient temperature for 18 hr. The reaction was checked by Reverse phase HPLC (Xterra 4.6×100 column, 0.1M TEAA/acetonitrile). The reaction volume was reduced to 200 μl by evaporation and the reaction was allowed to progress for 80 hr.

After 80 hr, the reaction was stopped by adding 15 ml 0.1 M TEAB. The diluted mixture was applied to a 19×100 Xterra RP column and eluted with an acetonitrile gradient in 0.1M TEAB. The fractions containing pure DDAO T4P were evaporated to dryness and coevaporated twice with ethanol. The residue was reconstituted with MilliQ water. Yield: 1.10 umole, 11%; HPLC purity>98% at 455 nm; MS: M−1=850.07 (calc. 849.95)

δ-9H(1,3-dichloro-9,9-dimethylacridin-2-one-7-yl)-deoxyguanosine-5'-tetraphosphate (dG4P-DDAO), δ-9H(1,3-dichloro-9,9-dimethylacridin-2-one-7-yl)-deoxycytidine-5'-tetraphosphate (dC4P-DDAO) and δ-9H(1,3-dichloro-9,9-dimethylacridin-2-one-7-yl)-deoxyadenosine-5'-tetraphosphate (dA4P-DDAO) were prepared in a similar manner as described above except 3.5 equivalents of DDAO phosphate was used instead of 8.3 equivalents. After C18 purification, samples were purified on ion exchange using a Mono Q 10/10 column.

δ-9H(1,3-dichloro-9,9-dimethylacridin-2-one-7-yl)-deoxyguanosine-5'-phosphate (dG4P-DDAO): Yield 0.57 umol, 5.7%; HPLC purity 99% at 455 nm; MS: M−1=875.03 (calc. 874.96).

δ-9H(1,3-dichloro-9,9-dimethylacridin-2-one-7-yl)-deoxycytidine-5'-tetraphosphate (dC4P-DDAO): Yield 0.24 umole, 2.4%; HPLC purity 99% at 455 nm; MS: M−1=835.03 (calc. 834.95).

δ-9H(1,3-dichloro-9,9-dimethylacridin-2-one-7-yl)-deoxyadenosine-5'-tetraphosphate (dA4P-DDAO): Yield 0.38 umole, 3.8%; HPLC purity 99% at 455 nm; MS: M−1=859.07 (calc. 858.97).

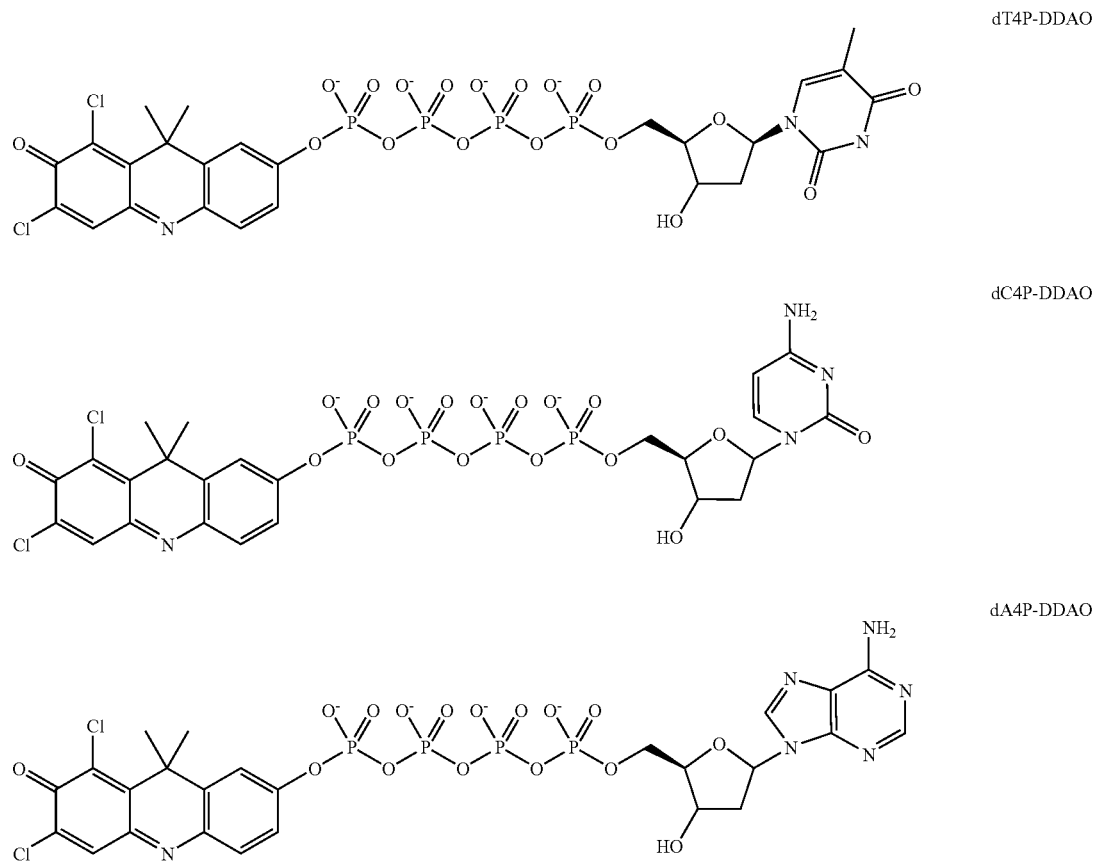

-continued

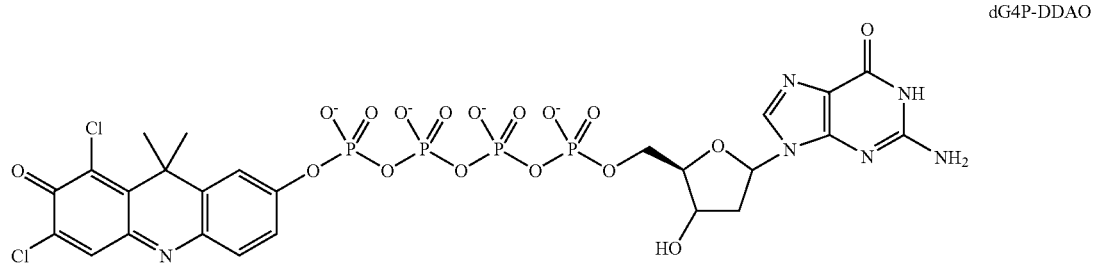

dG4P-DDAO

Example 5

Preparation of ε-9H (1,3-dichloro-9,9-dimethylacridin-2-one-7-yl)-dideoxythymidine-5'-pentaphosphate DDAO-ddT-pentaphosphate (ddT5P-DDAO)

A. Preparation of DDAO Pyrophosphate

DDAO-phosphate diammonium salt (11.8 umol) was coevaporated with anhydrous DMF (3×0.25 ml) and was dissolved in DMF (0.5 ml). To this carbonyldiimidazole (CDI, 9.6 mg, 5 eq) was added and the mixture was stirred at room temperature overnight. Excess CDI was destroyed by addition of MeOH (5 ul) and stirring for 30 minutes. To the mixture tributylammoniumdihydrogen phosphate (10 eq., 236 ml of 0.5 M solution in DMF) was added and the mixture was stirred at room temperature for 4 days. Reaction mixture was concentrated on rotavap. Residue was purified on HiPrep 16.10 Q XL column using 0–100% B using 0.1M TEAB/acetonitrle (3:1) as buffer A and 1 M TEAB/acetonitrile (3:1) as buffer B. Main peak (HPLC purity 98%) was collected, concentrated and coevaporated with methanol (2×). Residue was dissolved in 1 ml water to give 5.9 mM solution. UV/VIS $\lambda_{max}$=456 nm.

B. Preparation of ddT5P-DDAO ddTTP (100 ul of 47.5 mM solution in water) was coevaporated with anhydrous DMF (2×1 ml). To this DCC (5 eq., 4.9 mg) was added and mixture was coevaporated with DMF (1×1 ml). Residue was taken in anhydrous DMF (0.5 ml) and stirred at room temperature for 3 hours. To this 1.03 eq of DDAO pyrophosphate, separately coevaporated with anhydrous DMF (2×1 ml) was added as a DMF solution. Mixture was concentrated to dryness and then taken in 200 ul anhydrous DMF. Mixture was heated at 38° C. for 2 days. Reaction mixture was concentrated, diluted with water, filtered and purified on HiTrap 5 ml ion exchange column using 0–100% A-B using a two step gradient. Solvent A=0.1M TEAB/acetonitrile (3:1) and solvent B=1M TEAB/acetonitrile (3:1). Fraction 12×13 which contained majority of product were combined, concentrated and coevaporated with methanol (2×). Residue was repurified on Xterra RP C-18 30–100 mm column using 0.30% acetonitrile in 0.1M TEAB in 5 column and 30–50% acetonitrile in 2 column volumes, flow rate 10 ml/min. Fraction containing pure product was concentrated and coevaporated with methanol (2×) and water (1×). HPLC purity at 455 nm>99%. UV/VIS=268 nm and 455 nm. MS: M−1=914.03 (calc 913.93).

The DDAO dye attached to the gamma phosphate of these polyphosphates is fluorescent with an excitation maximum of 455 nm and an emission maximum of about 608 nm. Upon hydrolysis of the phosphate ester to release the free dye, the spectrum changes with excitation maximum of about 645 nm and emission maximum of about 659 nm. The change is readily detected by simple fluorescence measurements or color change.

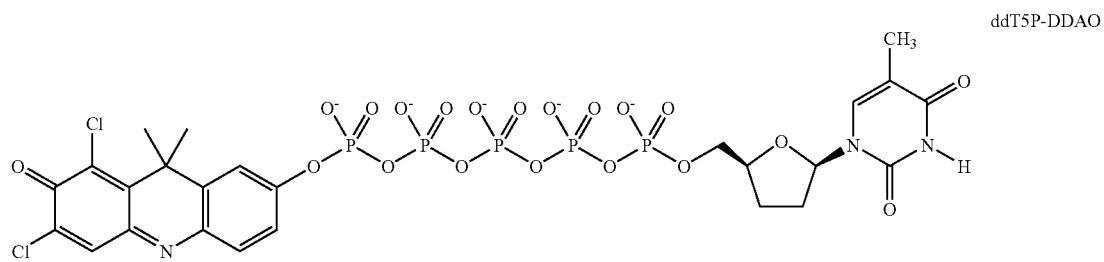

ddT5P-DDAO

It is noted that similar nucleotide compounds with dyes or other detectable moieties attached to the terminal phosphate could also be made using similar methods to those described in Examples 1–5 above. These include ribonucleotides, deoxyribonucleotides, dideoxynucleotides, nucleotides with any of the naturally-occurring bases (adenine, guanine, cytosine, thymine, hypoxanthine and uracil) as well as modified bases or modified sugars.

Examples 6, 7 and 8 below demonstrate that nucleotides with more than three phosphates having a dye derivative attached to the terminal phosphate are significantly better substrates than those with only three phosphates.

Example 6

Incorporation of ddTPn-DDAO, where n=3, 4 or 5, by a Polymerase

Reactions were assembled at room temperature (23° C.) using the dideoxynucleotides of Example (1–5). Reactions contained primer template combinations having a single oligonucleotide primer (represented by SEQ ID NO: 1) annealed to an oligonucleotide template corresponding to SEQ ID NO: 2.

Reaction conditions: A 70 µl reaction containing 50 mM Tris, pH 8.0, 5% glycerol, 5 mM MgCl$_2$, 0.01% tween-20, 0.21 units shrimp alkaline phosphatase, 100 nM primer annealed to template, and 1 µM ddTPn-DDAO was assembled in a quartz fluorescence ultra-microcuvet in a LS-55 Luminescence Spectrometer (Perkin Elmer), operated in time drive mode. Excitation and emission wavelengths are 620 nm and 655 nm respectively. Slit widths were 5 nm for excitation slits, 15 nm for emission slits. The reaction was initiated by the addition of 0.35 µl (11 units) of a cloned DNA polymerase I genetically engineered to eliminate 3'-5' exonuclease activity, 5'-3' exonuclease activity and discrimination against dideoxynucleotides and 0.25 mM MnCl$_2$.

As shown in FIG. 1, both tetra- and penta-phosphates are significantly better substrates than triphosphates.

Example 7

Comparison of the Rates of Incorporation of dTPn-DDAO, where n=3 or 4 by Different Polymerses Reactions were assembled at room temperature (23° C.) using the deoxynucleotides of Example (1–5). Reactions contained primer template combinations having a single oligonucleotide primer (represented by SEQ ID NO: 1) annealed to an oligonucleotide template corresponding to SEQ ID NO: 2.

Reaction conditions: A 70 µl reaction containing 50 mM Tris, pH 8.0, 5% glycerol, 5 mM MgCl$_2$, 0.01% tween-20, 0.25 units shrimp alkaline phosphatase, 100 nM primer annealed to template, and 1 µM ddTPn-DDAO was assembled in a quartz fluorescence ultra-microcuvet in a LS-55 Luminescence Spectrometer (Perkin Elmer), operated in time drive mode. Excitation and emission wavelengths are 620 nm and 655 nm respectively. Slit widths were 5 mm for excitation slits, 15 nm for emission slits. The reaction was initiated by the addition of 0.35 µl (11 units) of a cloned DNA polymerase I (genetically engineered to eliminate 3'-5' exonuclease activity, 5'-3' exonuclease activity and discrimination against dideoxynucleotides) or MMLV reverse transcriptase, and 0.25 mM MnCl$_2$.

Figure 2:
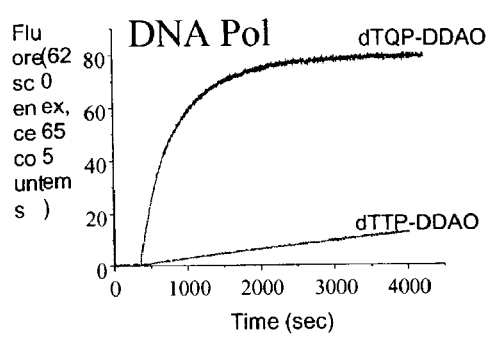
FIG. 2 presents a comparison of terminal phosphate labeled nucleoside tri- and tetra-phosphate incorporation by two different DNA polymerising enzymes
Figure 2:
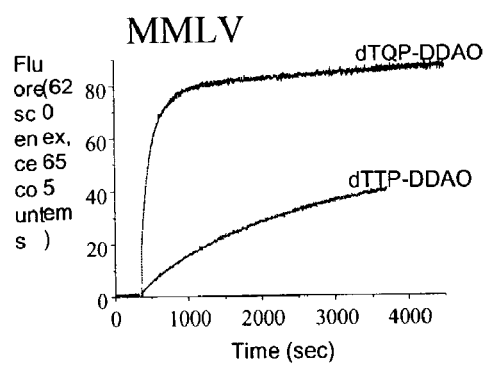

As shown in FIG. 2, with both polymerase and reverse transcriptase, the rate of incorporation of dT4P-DDAO is significantly higher than that of dT3P-DDAO.

Example 8

Incorporation of ddNPn-DDAO and ddNPn-Resorufin, where N is A,C,G or T and n=3 or 4

Reactions were assembled at room temperature (23° C.) using the dideoxynucleotides of Example (1–5). Reactions contained primer template combinations having a single oligonucleotide primer (represented by SEQ ID NO: 1) annealed to an oligonucleotide template corresponding to SEQ ID NO: 2–5 depending on the next base to be added.

Reaction conditions: A 70 µl reaction containing 50 mM Tris, pH 8.0, 5% glycerol, 5 mM MgCl$_2$, 0.01% tween-20, 0.21 units shrimp alkaline phosphatase, 100 nM primer annealed to template, and 1 µM ddTPn-DDAO was assembled in a quartz fluorescence ultra-microcuvet in a LS-55 Luminescence Spectrometer (Perkin Elmer), operated in time drive mode. Excitation and emission wavelengths are 620 nm and 655 nm respectively. Slit widths were 5 nm for excitation slits, 15 nm for emission slits. The reaction was initiated by the addition of 0.35 µl (11 units) of a cloned DNA polymerase I genetically engineered to eliminate 3'-5' exonuclease activity, 5'-3' exonuclease activity and discrimination against dideoxynucleotides and 0.25 mM MnCl$_2$.

Figure 3:
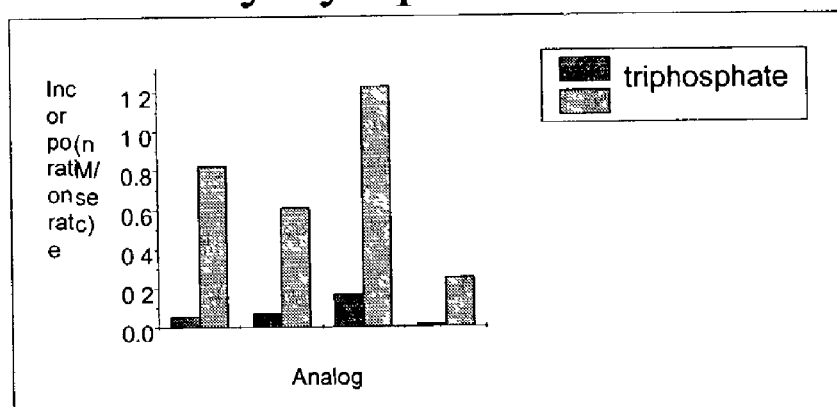
FIG. 3 presents differences in the rates of incorporation of two sets of terminal phosphate labeled nucleoside tri- and tetra-phosphates with all four different bases and two different dyes.
Figure 3:
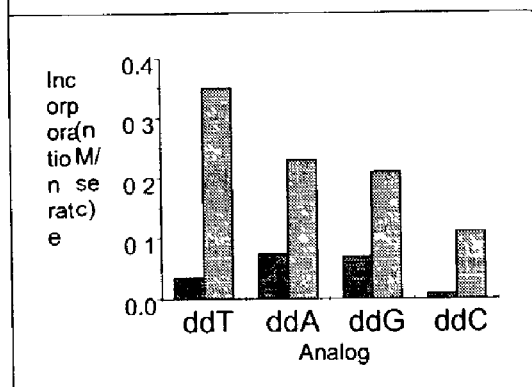

As apparent from FIG. 3, with all different bases as well as two different dyes investigated, the tetraphosphate analogs are significantly better incorporated than their triphosphate counterparts.

Having described the particular, desired embodiments of the invention herein, it should be appreciated that modifications may be made therethrough without departing from the contemplated scope of the invention. The true scope of the invention is set forth in the claims appended hereto.

What is claimed is:

1. A composition comprising a terminal phosphate labeled nucleoside polyphosphate of formula

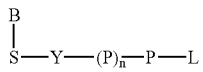

wherein P=phosphate ($PO_3$) and derivatives thereof, n is 3 or greater; Y is an oxygen or sulfur atom; B is a nitrogen-containing heterocyclic base; S is an acyclic moiety, a carbocyclic moiety, or sugar moiety; L is a fluorescent, a fluorogenic, a chemiluminescent, a colored, a chromogenic, a mass tag, or an electrochemical label with or without a linker containing a hydroxyl group, a sulfhydryl group, an amino group or a haloalkyl group suitable for forming a phosphate ester, a thioester, a phosphoramidate or an alkyl phosphonate linkage at the terminal phosphate of a natural or modified nucleotide.

2. The composition according to claim 1 wherein said labels are those selected from the group consisting of chemiluminescent compounds, fluorescent or fluorogenic dyes, colored or chromogenic dyes, electrochemical tags and combinations thereof.

3. The composition of claim 1 wherein n is three, four or five.

4. The composition of claim 1 wherein said label is selected from the group consisting of chemiluminescent compounds, fluorogenic dyes, chromogenic dyes, electrochemical tags and combinations thereof.

5. The composition of claim 1 wherein said L is detectable by a property selected from the group consisting of color, fluorescence emission, chemiluminescence, reduction/oxidation potential and combinations thereof.

6. The composition of claim 5 wherein said label is an enzyme-activatable fluorogenic moiety and P-L is selected from the group consisting of 2-(5'-chloro-2'-phosphoryloxyphenyl)-6-chloro-4-(3H)-quinazolinone, fluorescein diphosphate, fluorescein 3'(6')-O-alkyl-6'(3')-phosphate, 9H-(1,3-dichloro-9,9-dimethylacridin-2-one-7-yl)phosphate, 4-methylumbelliferyl phosphate, resorufin phosphate, 4-trifluoromethylumbelliferyl phosphate, umbelliferyl phosphate, 3-cyanoumbelliferyl phosphate, 9,9-dimethylacirdin-2-one-7-yl phosphate, 6,8-difluoro-4-methylumbelliferyl phosphate, and derivatives thereof.

7. The composition of claim 5 wherein the said label is a fluorescent moiety selected from the group consisting of fluorescein, rhodamine, bodipy™, cyanine, Alexa™, Naphthofluorescein, Oregon Green™, coumarin, dansyl, Texas Red™, pyrene, and derivatives thereof.

8. The composition of claim 5 wherein said label is an enzyme-activatable chromogenic moiety, and P-L is selected from the group consisting of p-nitrophenyl phosphate, dinitrophenol phosphate, oxonoly phosphate, merrocyanine phosphate and derivatives thereof.

9. The composition of claim 5 wherein said chemiluminescent compound is a phosphatase-activated 1,2-dioxetane compound.

10. The composition of claim 1 wherein P-L is selected from the group consisting of 2-chloro-5-(4-methoxyspiro[1,2-dioxetane-3,2'-(5-chloro-)tricyclo[3,3,1-1$^{3,7}$]-decan]-1-yl)-1-phenyl phosphate, chloroadamant-2'-ylidenemethoxyphenoxy phosphorylated dioxetane, 3-(2'-spiroadamantane)-4-methoxy-4-(3"-phosphoryloxy)phenyl-1,2-dioxetane and derivatives thereof.

11. The composition of claim 1 wherein said sugar moiety is selected from the group consisting of ribosyl, 2'-deoxyribosyl, 3'-deoxyribosyl, 2',3'-dideoxyribosyl, 2',3'-didehydrodideoxyribosyl, 2'-alkoxyribosyl, 2'- or 3'-azidoribosyl, 2'- or 3'-aminoribosyl, 2'- or 3'-fluororibosyl, 2'-mercaptoriboxyl, 2'-alkylthioribosyl, carbocyclic, acyclic and other modified sugars.

12. The composition of claim 1 wherein said base is selected from the group consisting of uracil, thymine, cytosine, 5-methylcytosine, guanine, 7-deazaguanine, hypoxanthine, 7-deazahypoxanthine, adenine, 7-deazaadenine, 2,6-diaminopurine and analogs thereof.

13. The composition of claim 1, which is a substrate for a nucleic acid polymerase.

14. The composition of claim 1 wherein L interacts with additional chemical and/or enzymatic moieties to generate a signal.

15. A method of detecting the presence of a DNA sequence comprising the steps of:
a) conducting a DNA polymerase reaction in the presence of a terminal-phosphate-labeled nucleotide containing at least four phosphates, which reaction results in the production of a labeled polyphosphate;
b) permitting said labeled polyphosphate to react with a phosphate or polyphosphate transferring enzyme to produce a detectable species; and
c) detecting the presence of said detectable species.

16. The method of claim 15 wherein step (a) further includes conducting said polymerase reaction in the presence of a phosphate or polyphosphate transferring enzyme.

17. The method of claim 15 wherein step (a) further includes conducting said polymerase reaction in the presence of two or more terminal-phosphate-labeled nucleotides with distinct labels.

18. The method of claim 15 wherein said labels are enzyme-activatable labels selected from the group consisting of chemiluminescent compounds, fluorogenic or fluorescent dyes, chromogenic or colored dyes, mass tags, electrochemical tags and combinations thereof.

19. The method of claim 15 wherein said terminal-phosphate-labeled nucleotide may be represented by formula I:

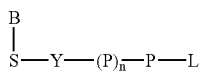

wherein P=phosphate (PO$_3$) and derivatives thereof, n is 3 or greater; Y is an oxygen or sulfur atom; B is a nitrogen-containing heterocyclic base; S is an acyclic moiety, a carbocyclic moiety or sugar moiety; L is a fluorescent, a fluorogenic, a chemiluminescent, a colored, a chromogenic, an electrochemical, or mass tag with or without a linker containing a hydroxyl group, a sulfhydryl group, or an amino group suitable for forming a phosphate ester, a thioester, or a phosphoramidate at the terminal phosphate of a natural or modified nucleotide.

20. The method of claim 19 wherein n is three, four or five.

21. The method of claim 15 further comprising the step of quantifying said DNA sequence.

22. The method of claim 15 wherein said detectable species is produced in amounts substantially proportional to the amount of sequence.

23. The method of claim 15 further comprising the step of including one or more additional detection reagents in said polymerase reaction.

24. The method of claim 23 wherein said additional detection reagents are capable of a response that is detectably different from said detectable species.

25. The method of claim 23 wherein said additional detection reagent is an antibody.

26. A nucleic acid detection kit comprising:
(a) at least one or more terminal-phosphate-labeled nucleotides of claim 1;
(b) at least one of the enzymes selected from the group consisting of DNA polymerase, RNA polymerase and reverse transcriptase; and
(c) a phosphate or polyphosphate transferring enzyme.

27. The kit of claim 26 wherein n is three, four or five.

28. The kit of claim 26 wherein said sugar moiety is selected from the group consisting of ribosyl, 2'-deoxyribosyl, 3'-deoxyribosyl, 2',3'-didehydrodideoxyribosyl, 2',3'-dideoxyribosyl, 2'-alkoxyribosyl, 2'- or 3'-azidoribosyl, 2'- or 3'-aminoribosyl, 2'- or 3'-fluororibosyl, 2'-mercaptoribosyl, 2'-alkylthioribosyl, carbocyclic, acyclic and other modified sugars.

29. The kit of claim 26 wherein said base is selected from the group consisting of uracil, thymine, cytosine, 5-methylcytosine, guanine, 7-deazaguanine, hypoxanthine, 7-deazahypoxanthine, adenine, 7-deazaadenine, 2,6-diaminopurine and analogs thereof.

30. The kit of claim 26 wherein said label is selected from the group consisting of chemiluminescent compounds, fluorogenic dyes, chromogenic dyes, mass tags, electrochemical tags and combinations thereof.

31. The method of claim 15 wherein step (b) is omitted and the detectable species in step (c) is labeled polyphosphate.

* * * * *

UNITED STATES PATENT AND TRADEMARK OFFICE
CERTIFICATE OF CORRECTION

PATENT NO. : 7,041,812 B2 Page 1 of 1
APPLICATION NO. : 10/230576
DATED : May 9, 2006
INVENTOR(S) : Shiv Kumar It is certified that error appears in the above-identified patent and that said Letters Patent is hereby corrected as shown below:

Column 1,
Line 4-5, after "This application" delete "is a provisional of Ser. No. 60/315,798 filed Aug. 29, 2001."

Column 1,
Line 4-5, after "This application" add -- claims priority benefit under Title 35 §119(e) of U.S. Provisional Application No. 60/315,798, filed August 29, 2001. --

Signed and Sealed this

Thirteenth Day of May, 2008

JON W. DUDAS
*Director of the United States Patent and Trademark Office*